United States Patent
Tunnacliffe et al.

(10) Patent No.: US 6,468,782 B1
(45) Date of Patent: *Oct. 22, 2002

(54) METHODS OF PRESERVING PROKARYOTIC CELLS AND COMPOSITIONS OBTAINED THEREBY

(75) Inventors: Alan G. Tunnacliffe, Horningsea; David T. Welsh, Stanley; Bruce J. Roser, Cambridge; Kamaljit S. Dhaliwal, Hitchin; Camilo Colaco, Cambridge, all of (GB)

(73) Assignee: Quadrant Healthcare (UK) Limited, Nottingham (GB)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/985,343

(22) Filed: Dec. 4, 1997

Related U.S. Application Data

(60) Provisional application No. 60/032,423, filed on Dec. 5, 1996.

(51) Int. Cl.$^7$ .................................................. C12N 1/04
(52) U.S. Cl. ........................................ 435/260; 435/244
(58) Field of Search .................................. 435/244, 260

(56) References Cited

U.S. PATENT DOCUMENTS

| | | |
|---|---|---|
| 4,436,728 A | 3/1984 | Ribi et al. |
| 4,620,847 A | 11/1986 | Sishov et al. |
| 4,684,719 A | 8/1987 | Nishikawa et al. |
| 4,726,947 A | 2/1988 | Shimada et al. |
| 4,793,997 A | 12/1988 | Drake et al. |
| 4,814,436 A | 3/1989 | Shibata et al. |
| 4,855,326 A | 8/1989 | Fuisz |
| 4,891,319 A | 1/1990 | Roser |
| 5,026,566 A | 6/1991 | Roser |
| 5,057,540 A | 10/1991 | Kensil et al. |
| 5,077,284 A | 12/1991 | Loria et al. |
| 5,149,653 A | 9/1992 | Roser |
| 5,171,568 A | 12/1992 | Burke et al. |
| 5,306,506 A | 4/1994 | Zema et al. |
| 5,380,473 A | 1/1995 | Bogue et al. |
| 5,387,431 A | 2/1995 | Fuisz |
| 5,407,684 A | 4/1995 | Loria et al. |
| 5,425,951 A | 6/1995 | Goodrich, Jr. et al. |
| 5,512,547 A | 4/1996 | Johnson et al. |
| 5,567,439 A | 10/1996 | Myers et al. |
| 5,589,167 A | 12/1996 | Cleland et al. |
| 5,728,574 A | 3/1998 | Legg |
| 5,766,520 A * | 6/1998 | Bronshtein .................. 435/188 |
| 5,780,295 A * | 7/1998 | Livesey et al. ........... 435/307.1 |

FOREIGN PATENT DOCUMENTS

| | | |
|---|---|---|
| EP | 0139286 | 5/1985 |
| EP | 0357665 | 3/1994 |
| EP | 0601965 | 6/1994 |
| EP | 0 639 645 A1 | 2/1995 |
| EP | 0714905 | 6/1996 |
| FR | 2238476 | 3/1975 |
| GB | 1381588 | 1/1975 |
| JP | 58-216695 | 12/1983 |
| JP | 63-502592 | 9/1988 |
| WO | WO 87/00196 | 1/1987 |
| WO | WO 90/11756 | 10/1990 |
| WO | WO 91/16924 | 11/1991 |
| WO | WO 92/16231 | 10/1992 |
| WO | WO 93/02834 | 2/1993 |
| WO | WO 93/10758 | 6/1993 |
| WO | WO 93-11220 | 6/1993 |
| WO | WO 93/23110 | 11/1993 |
| WO | WO 94/24263 | 10/1994 |
| WO | WO 95/03395 | 2/1995 |
| WO | WO 95/06126 | 3/1995 |
| WO | WO 96/05809 | 2/1996 |
| WO | WO 96/40077 | 12/1996 |

OTHER PUBLICATIONS

Kachura, "Method of Drying Lactic Acid Bacteria", Vinodelie i Vinogradarstvo SSSR (1985) 2:49–50.*

Hatley et al., "Stabilization of labile materials by amorphous carbohydrates–glass fragility and the physiochemical properties that make trehalose a superior excipient", Pharmaceutical Research 13 (9 Supp.) S274 (1996).*

Blakeley et al., "Dry instant blood typing plate for bedside use" (1990) *Lancet* 336:854–855.

Colaco et al., "Extraordinary stability of enzymes dried in trehalose: Simplified molecular biology" (1992) *Bio/Tech.* 10:1007–1011.

Colaco et al., "Trehalose stabilisation of biological molecules" (1992) *Biotechnol. Internat.* 1:345–350.

Crowe et al., "Are freezing and dehydration similar stress vectors? A comparison of modes of interaction of stabilizing solutes with biomolecules" (1990) *Cryobiol.* 27:219–231.

Dinnbier et al., "Transient accumulation of potassium glutamate and its replacement by trehalose during adaption of growing cells of *Escherichia coli* K–12 to elevated sodium chloride concentrations" (1988) *Arch. Microbiol.* 150:348–357.

(List continued on next page.)

Primary Examiner—Sandra E. Saucier
(74) Attorney, Agent, or Firm—Morrison & Forester LLP

(57) ABSTRACT

This invention provides methods of drying and stabilizing prokaryotic cells, and the compositions obtained thereby. The cells are first cultured or incubated under conditions sufficient to induce intracellular trehalose, suspended in a stabilizing solution and dried to form a solid glass. The resulting product is storage-stable at room temperature, showing little viability loss on storage.

23 Claims, 8 Drawing Sheets

OTHER PUBLICATIONS

Giæver et al., "Biochemical and genetic characterization of osmoregulatory trehalose synthesis in *Escherichia coli*" (1988) *J. Bacterial.* 170:2841–2849.

Israeli et al., "Protection of freeze–dried *Escherichia coli* by trehalose upon exposure to environmental conditions" (1993) *Cryobiol.* 30:519–523.

Larsen et al., "Osmoregulation in *Escherichia coli* by accumulation of organic osmolytes: betaines, glutamic acid and trehalose" (1987) *Arch. Microbiol.* 147:1–7.

Leslie et al., "Trehalose and sucrose protect both membranes and proteins in intact bacteria during drying" (1995) *Appl. Env. Microbiol.* 61:3592–3597.

Louis et al., "Survival of *Escherichia coli* during drying and storage in the presence of compatible solutes" (1994) *Appl. Microbiol. Biotechnol.* 41:684–688.

Potts, "Desiccation tolerance of prokaryotes" (1994) *Micro. Rev.* 58:755–805.

Roser, "Trehalose drying: A novel replacement for freeze–drying" (1991) *BioPharm.* 4:47–53.

Roser, "Trehalose, a new approach to premium dried foods" (1991) *Trends in Food Sci. and Tech.* 10:166–169.

Roser et al., "A sweeter way to fresher food" (May 1993) *New Scientist*, pp. 25–28.

Takahashi et al., "Induction of CD8$^+$ cytotoxic T cells by immunization with purified HIV–1 envelope protein in ISCOMs" (1990) *Nature* 344:873–875.

Welsh et al., "The role of trehalose in the osmoadaptation of *Escherichia coli* NCIB 9484: interaction of trehalose, K$^+$ and glutamate during osmoadaptation in continuous culture" (1991) *J. Gen. Microbiol.* 137:745–750.

Abstract of JP 58–216695 (Dec. 16, 1983).

Abstract of FR 2238476 (Mar. 28, 1975).

Abstract of JP 63–502592 (Sep. 29, 1988).

Kanna et al., "Denaturation of Fish Muscle Protein by Dehydration—V." *Bull. Tokai Reg. Fish. Res. Lab.* (1974) 77:1–17.

*Development of a dry and thermostable oral polio vaccine*, Progress Report QHCL, RIVM and RUG, May 1993–Oct. 1993, (Apr. 22, 1994).

*Develoment of a dry and thermostable oral polio vaccine*, Progress Report QHCL and RIVM Nov. 1993–Apr. 1994, (Apr. 22, 1994).

*Stability and characterization of protein and peptide drugs*, Wang et al. (eds.), 1993, Table of contents enclosed herewith.

Strom, A. R. and Kaasen, I. (1993). "Trehalose Metabolism in *Escherichia coli*: Stress Protection and Stress Regulation of Gene Expression," *Molecular Microbiology* 8(2):205–210.

Welsh, D. T. (Aug. 1992). "The Role of Compatible Solutes in the Adaptation and Survival of *Escherichia coli*," Ph.D. Thesis Submitted to Department of Biological Sciences, University of Dundee. Pp. 1–262.

\* cited by examiner

```
  1  ----MVNQDISKLSLNECPGSVIVISNRLPVTIKKDEXTGEYEYSMSSGGLVTALQG
  1  ----MTTDNAKAQLTSSSGGNIVVVSNRLPVTITKNSSTGQYEYAMSSGGLVTALEG
  1  ------MPSLENPTFQNEARLLLVSNRLPITIKRSDD-GRYDFSMSSGGLVSGLSG
  1  MSDAHDTIKSLTGDA-SNSRRLIVVSNRLPITIKRKDN-GTYDFSMSSGGLVSALSG
  1  MTSRGNHGSKTSSDKHLGDSDFVVVANRLPVDQVRLPD-GTAIWKRSPGGLVTALEP
  1  ----------------SRLVVVSNRIA---------PPDEHAASAGGLAVGILG

54  LKRSTTFQWYGWPGLEVPDEDKAK-VKRELEKFNAIPIFLSDEVADLHYNGFSNSI
 54  LKKTYTFKWFGWPGLEIPDDEKDQ-VRKDLLEKFNAVPIFLSDEIADLHYNGFSNSI
 50  LSKSTTFQWIGWPGLEVPEEEIPV-VKERLKQEYNAVPVFLDDELADRHYNGFSNSI
 56  LKRLHTFQWLGWCGQEIPEDEKPH-IIQRLQDECSAIPVFLDDETADRHYNGFSNSI
 57  LLRQRRGAWVGWPGVINDNVDLDLTIKSIVQDGLTLYPVRLNTHDVAEYTEGFSNAT
 30  ALKAAGGLWFGHSGETGNEDQPLKKVKK---GNITWASFNLSEQDLDEYIMQFSNAV

110  LWPLFHYHPGEITFDDTAWLATNEANMAFADEIEGNINDNDVVWVHDYHLMLLPEMI
110  LWPLFHYHPGEINFDENAWLATNEANQTFTNEIAKTHNENDLIWVHDYHLMLVPEML
106  LWPLFHYHPGEITFDESAWDATKEANRLFAKAVAKEVQDGDLIWVHDYHLMLLPEML
112  LWPLFHYHPGEINFDEENWLATRAANYAFAEIVKNLQDGQLIWVQDIHLMVLPQML
114  LWPLTHDVIVKPIYHCEWWERYVDVNRRFAETSRTAAYGGTVWVQDIQLQLVPKML
 84  LWPAFHYRLDLVQFQRPAWDGTLRVNALLADKLLPLLQDDEITWIHDYHLLPFAHEL

167  RQRVIAKKLKNIKIGWFLHTPFPSSEIYRILPVRQEILKGVLSCDLIGFHTYDYARH
167  RVKIHEKQLQNVKVGWFLHTPFPSSEIYRILPVRQZILKGVLSCDLVGFHTYDYARH
163  REEI-GDSKENVKIGFFLHTPFPSSEIYRILPVRNELLLGVLHCDLIGFHTYDYTRH
169  RELI-GDKFKDIKIGFFLHTPFPSSEIYRLPVRNEILEGVLNCDLVGFHTYDYARH
171  RIM-----RPDLTIGFFLHTPFPVDLFHQIHWRTEIIEGLLGADLVGFHLTSGAQN
141  R------KRGVNNRIGFFLBIPFPTPEIFNALHTIDTLLEQLCDIDLLGFQTENDRLA

224  FLSAVQRILNVNTLP---------NGVEFDGRFVNVGAFPIGIDVETFTEGLKQDAV
224  FLSSVQRVLNVNTLP---------NGVEIQGRFVNVGAFPIGIDVDKFTDGLKKESV
219  FLSACSRLLGLTTTP---------NGIEFQGKIIACGAFPIGIDPEKFEEGLKKEKV
225  FLSACSRILNLSTLP---------NGVEINGQHVSVGTFPIGIDPEKFSDALKSDVV
223  FLFLSRHLLGANTSRGLVGVRSRFGEVQLKSHTVQVGAFPISIDSKEIDQATRDRNV
193  FLDCLSNLTRVTTRSAKSHTAW--------GKAFRTEVYPIGIEPKEIAKQA-AGPL

272  IKRIKELKESFKGC-KIIIGVDRLDTIKGVPQKLHALEVFLGAHPEWIGKVVLVQVA
272  QKRIQQLKETFKGC-KIIVGVDRLDIIKGVPQKLHAMEVFLNEHPEWRGKVVLVQVA
267  QKRIAMLEQKFQGV-KLKVGVDRLDYIKGVPQKLHALEVFLSDHPEWVGKVVLVQVA
273  KDRIRSIERRLQGV-KVIVGVDRLDYIKGVPQKFHAIEVFLEQTPEWVGKVVLVQVA
280  RRRAREIRAELGNPRKILLGVDRLDTIKGIDVRLRAFAELLAEGRAKRDDTVLVQIA
241  PPKLAQLKAELKNVQNIF-SVERLDTSKGLPERFLATEALLEKTPQHHGKIRYTQIA

328  VPSRGDVEEIQTLRSVVNELVGRINGQFGTAEFVPIHFMHRSIPFQELISLTAVSDV
328  VPSRGDVEEIQILRSVVNELVGRINGQFGTVEFVPIHFMRNSIPFEELISLIAVSDV
323  VPSRQDVEEIQMLRAVVNELVGRINGKFGTVEFMPIHFLRNSVNFDELIALYAVSDA
329  VPSRQDVEEIQNLRAVVNELVGRINGRFGTVEITPIHFLRNSVRFEBLVALYNVSDV
337  TPSREFVESTKILRNDIERQVGEINGEYGEVGHPVVHTLERPIPRDELIAFYVASDV
297  PTSRGDVQAYQDTRHQLENEAGRINGKTGQLGWTPLTYLNQHFDRKLLMKIFRYSDV

385  CLVSSTRDGMNLVSIEYISCQE-EKNGTLILSEFTGAAQSLNGALIVNPWNTDDLAE
385  CLVSSTRDGMNLVSIEYIACQE-EKNGSLILSEFTGAAQSLNGAIIVNPWNTDDLSD
380  CIVSSTRDGMNLVATEYIATQK-KRHGVLVLSEFAGAAQSLNGSILINPWNTEELAG
386  CLITSTRDGMNLVSIEYICTQQ-ERHGALILSEFAGAAQSLNGSIVINPWNTEELAN
394  MLVTPLRDGMNLVAKEIVACRN-DLGGALVLSEFTGAAELRQAYLVNPHDLEGVKD
354  GLVTPLRDGMNLVAKETVAAQDPANPGVLVLSQFAGAANELTSALIVNPYDRDEVAA

441  SINEALTVPEEKRAANWEKLYKTISKYTSAFWGENFVHELYRLGSSNN---------
441  AINEALTLPDVKKEVNWEKLYKYISKYTSAFWGENFVHELYSTSSSSTSSSATKN--
436  AIQEAVTMSDEQRALNFSKLDKYVNKITSAFWGQSFVTELTRISEHSAEKFHAKKAS
442  SIHDALTMPEKQREANEKLFRIVMKITSQFWGPKLCR---------------------
450  TIEAALNQLAEEARRRMRSLRRQVLAEDVDRWARSFLDALAEAPARDAT---------
411  ALDRALTMSLAERISRHAEMLDVIVKNDINHWQECFISDLKQIVPRSAESQQRDKVA

0  ------------------------
  0  ------------------------
493  FSDNNSENGEPSNGVETPAQEQVAQ
  0  ------------------------
  0  ------------------------
468  TFPKLA------------------
```

FIG.1

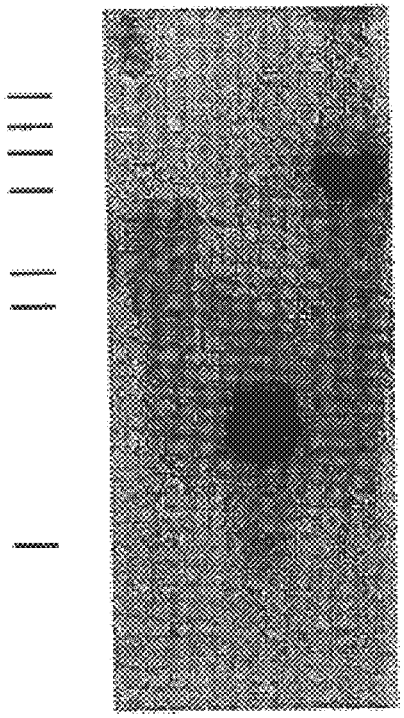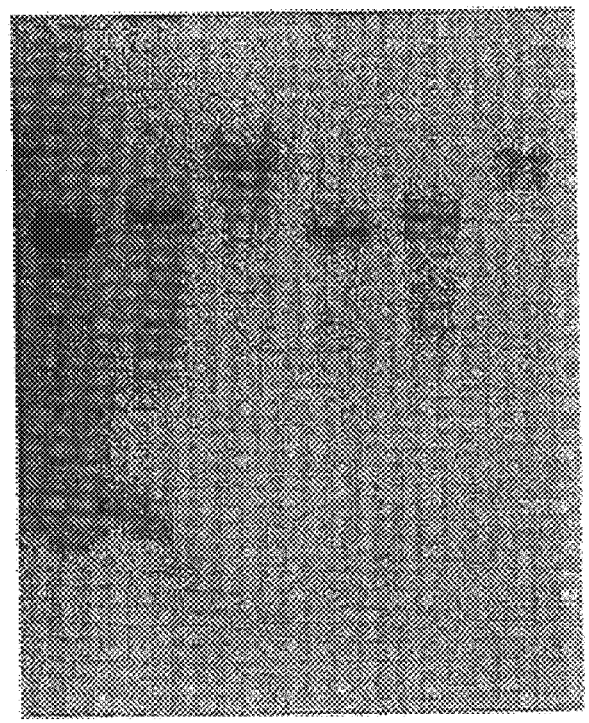
FIG. 2

● [Tre]ᵢ
■ Protein concentration

SEQUENCE LISTING (1) GENERAL INFORMATION:

(iii) NUMBER OF SEQUENCES: 6

(2) INFORMATION FOR SEQ ID NO:1:

(i) SEQUENCE CHARACTERISTICS:
      (A) LENGTH: 488 amino acids
      (B) TYPE: amino acid
      (C) STRANDEDNESS: single
      (D) TOPOLOGY: linear (xi) SEQUENCE DESCRIPTION: SEQ ID NO:1:

```
Met Val Asn Gln Asp Ile Ser Lys Leu Ser Leu Asn Glu Cys Pro Gly
1               5                   10                  15

Ser Val Ile Val Ile Ser Asn Arg Leu Pro Val Thr Ile Lys Lys Asp
                20                  25                  30

Glu Lys Thr Gly Glu Tyr Glu Tyr Ser Met Ser Ser Gly Gly Leu Val
            35                  40                  45

Thr Ala Leu Gln Gly Leu Lys Lys Ser Thr Thr Phe Gln Trp Tyr Gly
        50                  55                  60

Trp Pro Gly Leu Glu Val Pro Asp Glu Asp Lys Ala Lys Val Lys Arg
65                  70                  75                  80

Glu Leu Leu Glu Lys Phe Asn Ala Ile Pro Ile Phe Leu Ser Asp Glu
                85                  90                  95

Val Ala Asp Leu His Tyr Asn Gly Phe Ser Asn Ser Ile Leu Trp Pro
                100                 105                 110

Leu Phe His Tyr His Pro Gly Glu Ile Thr Phe Asp Asp Thr Ala Trp
            115                 120                 125

Leu Ala Tyr Asn Glu Ala Asn Met Ala Phe Ala Asp Glu Ile Glu Gly
        130                 135                 140

Asn Ile Asn Asp Asn Asp Val Val Trp Val His Asp Tyr His Leu Met
145                 150                 155                 160

Leu Leu Pro Glu Met Ile Arg Gln Arg Val Ile Ala Lys Lys Leu Lys
                165                 170                 175

Asn Ile Lys Ile Gly Trp Phe Leu His Thr Pro Phe Pro Ser Ser Glu
                180                 185                 190

Ile Tyr Arg Ile Leu Pro Val Arg Gln Glu Ile Leu Lys Gly Val Leu
            195                 200                 205

Ser Cys Asp Leu Ile Gly Phe His Thr Tyr Asp Tyr Ala Arg His Phe
```

```
           210                 215                 220
Leu Ser Ala Val Gln Arg Ile Leu Asn Val Asn Thr Leu Pro Asn Gly
225                 230                 235                 240

Val Glu Phe Asp Gly Arg Phe Val Asn Val Gly Ala Phe Pro Ile Gly
                245                 250                 255

Ile Asp Val Glu Thr Phe Thr Glu Gly Leu Lys Gln Asp Ala Val Ile
                260                 265                 270

Lys Arg Ile Lys Glu Leu Lys Glu Ser Phe Lys Gly Cys Lys Ile Ile
                275                 280                 285

Ile Gly Val Asp Arg Leu Asp Tyr Ile Lys Gly Val Pro Gln Lys Leu
    290                 295                 300

His Ala Leu Glu Val Phe Leu Gly Ala His Pro Glu Trp Ile Gly Lys
305                 310                 315                 320

Val Val Leu Val Gln Val Ala Val Pro Ser Arg Gly Asp Val Glu Glu
                325                 330                 335

Tyr Gln Tyr Leu Arg Ser Val Val Asn Glu Leu Val Gly Arg Ile Asn
                340                 345                 350

Gly Gln Phe Gly Thr Ala Glu Phe Val Pro Ile His Phe Met His Arg
                355                 360                 365

Ser Ile Pro Phe Gln Glu Leu Ile Ser Leu Tyr Ala Val Ser Asp Val
    370                 375                 380

Cys Leu Val Ser Ser Thr Arg Asp Gly Met Asn Leu Val Ser Tyr Glu
385                 390                 395                 400

Tyr Ile Ser Cys Gln Glu Lys Lys Gly Thr Leu Ile Leu Ser Glu
                405                 410                 415

Phe Thr Gly Ala Ala Gln Ser Leu Asn Gly Ala Leu Ile Val Asn Pro
                420                 425                 430

Trp Asn Thr Asp Asp Leu Ala Glu Ser Ile Asn Glu Ala Leu Thr Val
                435                 440                 445

Pro Glu Glu Lys Arg Ala Ala Asn Trp Glu Lys Leu Tyr Lys Tyr Ile
    450                 455                 460

Ser Lys Tyr Thr Ser Ala Phe Trp Gly Glu Asn Phe Val His Glu Leu
465                 470                 475                 480

Tyr Arg Leu Gly Ser Ser Asn Asn
                485

(2) INFORMATION FOR SEQ ID NO:2:

(i) SEQUENCE CHARACTERISTICS:
        (A) LENGTH: 495 amino acids
        (B) TYPE: amino acid
        (C) STRANDEDNESS: single
        (D) TOPOLOGY: linear (xi) SEQUENCE DESCRIPTION: SEQ ID NO:2:

Met Thr Thr Asp Asn Ala Lys Ala Gln Leu Thr Ser Ser Ser Gly Gly
1               5                   10                  15

Asn Ile Val Val Ser Asn Arg Leu Pro Val Thr Ile Thr Lys Asn
                20                  25                  30

Ser Ser Thr Gly Gln Tyr Glu Tyr Ala Met Ser Ser Gly Gly Leu Val
            35                  40                  45

Thr Ala Leu Glu Gly Leu Lys Lys Thr Tyr Thr Phe Lys Trp Phe Gly
    50                  55                  60

Trp Pro Gly Leu Glu Ile Pro Asp Asp Glu Lys Asp Gln Val Arg Lys
65                  70                  75                  80
```

-continued

```
Asp Leu Leu Glu Lys Phe Asn Ala Val Pro Ile Phe Leu Ser Asp Glu
                 85                  90                  95

Ile Ala Asp Leu His Tyr Asn Gly Phe Ser Asn Ser Ile Leu Trp Pro
            100                 105                 110

Leu Phe His Tyr His Pro Gly Glu Ile Asn Phe Asp Glu Asn Ala Trp
        115                 120                 125

Leu Ala Tyr Asn Glu Ala Asn Gln Thr Phe Thr Asn Glu Ile Ala Lys
    130                 135                 140

Thr Met Asn His Asn Asp Leu Ile Trp Val His Asp Tyr His Leu Met
145                 150                 155                 160

Leu Val Pro Glu Met Leu Arg Val Lys Ile His Glu Lys Gln Leu Gln
                165                 170                 175

Asn Val Lys Val Gly Trp Phe Leu His Thr Pro Phe Pro Ser Ser Glu
            180                 185                 190

Ile Tyr Arg Ile Leu Pro Val Arg Gln Glu Ile Leu Lys Gly Val Leu
        195                 200                 205

Ser Cys Asp Leu Val Gly Phe His Thr Tyr Asp Tyr Ala Arg His Phe
    210                 215                 220

Leu Ser Ser Val Gln Arg Val Leu Asn Val Asn Thr Leu Pro Asn Gly
225                 230                 235                 240

Val Glu Tyr Gln Gly Arg Phe Val Asn Val Gly Ala Phe Pro Ile Gly
                245                 250                 255

Ile Asp Val Asp Lys Phe Thr Asp Gly Leu Lys Lys Glu Ser Val Gln
            260                 265                 270

Lys Arg Ile Gln Gln Leu Lys Glu Thr Phe Lys Gly Cys Lys Ile Ile
        275                 280                 285

Val Gly Val Asp Arg Leu Asp Tyr Ile Lys Gly Val Pro Gln Lys Leu
    290                 295                 300

His Ala Met Glu Val Phe Leu Asn Glu His Pro Glu Trp Arg Gly Lys
305                 310                 315                 320

Val Val Leu Val Gln Val Ala Val Pro Ser Arg Gly Asp Val Glu Glu
                325                 330                 335

Tyr Gln Tyr Leu Arg Ser Val Val Asn Glu Leu Val Gly Arg Ile Asn
            340                 345                 350

Gly Gln Phe Gly Thr Val Glu Val Pro Ile His Phe Met His Lys
        355                 360                 365

Ser Ile Pro Phe Glu Glu Leu Ile Ser Leu Tyr Ala Val Ser Asp Val
    370                 375                 380

Cys Leu Val Ser Ser Thr Arg Asp Gly Met Asn Leu Val Ser Tyr Glu
385                 390                 395                 400

Tyr Ile Ala Cys Gln Glu Glu Lys Lys Gly Ser Leu Ile Leu Ser Glu
                405                 410                 415

Phe Thr Gly Ala Ala Gln Ser Leu Asn Gly Ala Ile Ile Val Asn Pro
            420                 425                 430

Trp Asn Thr Asp Asp Leu Ser Asp Ala Ile Asn Glu Ala Leu Thr Leu
        435                 440                 445

Pro Asp Val Lys Lys Glu Val Asn Trp Glu Lys Leu Tyr Lys Tyr Ile
    450                 455                 460

Ser Lys Tyr Thr Ser Ala Phe Trp Gly Glu Asn Phe Val His Glu Leu
465                 470                 475                 480

Tyr Ser Thr Ser Ser Ser Thr Ser Ser Ala Thr Lys Asn
                485                 490                 495
```

(2) INFORMATION FOR SEQ ID NO:3:

(i) SEQUENCE CHARACTERISTICS:
        (A) LENGTH: 517 amino acids
        (B) TYPE: amino acid
        (C) STRANDEDNESS: single
        (D) TOPOLOGY: linear (xi) SEQUENCE DESCRIPTION: SEQ ID NO:3:

```
Met Pro Ser Leu Glu Asn Pro Thr Phe Gln Asn Glu Ala Arg Leu Leu
 1               5                  10                  15

Leu Val Ser Asn Arg Leu Pro Ile Thr Ile Lys Arg Ser Asp Asp Gly
                20                  25                  30

Arg Tyr Asp Phe Ser Met Ser Ser Gly Gly Leu Val Ser Gly Leu Ser
            35                  40                  45

Gly Leu Ser Lys Ser Thr Thr Phe Gln Trp Tyr Gly Trp Pro Gly Leu
 50                  55                  60

Glu Val Pro Glu Glu Glu Ile Pro Val Val Lys Glu Arg Leu Lys Gln
 65                  70                  75                  80

Glu Tyr Asn Ala Val Pro Val Phe Ile Asp Asp Glu Leu Ala Asp Arg
                85                  90                  95

His Tyr Asn Gly Phe Ser Asn Ser Ile Leu Trp Pro Leu Phe His Tyr
            100                 105                 110

His Pro Gly Glu Ile Thr Phe Asp Glu Ser Ala Trp Glu Ala Tyr Lys
        115                 120                 125

Glu Ala Asn Arg Leu Phe Ala Lys Ala Val Ala Lys Glu Val Gln Asp
        130                 135                 140

Gly Asp Leu Ile Trp Val His Asp Tyr His Leu Met Leu Leu Pro Glu
145                 150                 155                 160

Met Leu Arg Glu Glu Ile Gly Asp Ser Lys Glu Asn Val Lys Ile Gly
                165                 170                 175

Phe Phe Leu His Thr Pro Phe Pro Ser Ser Glu Ile Tyr Arg Ile Leu
            180                 185                 190

Pro Val Arg Asn Glu Leu Leu Leu Gly Val Leu His Cys Asp Leu Ile
        195                 200                 205

Gly Phe His Thr Tyr Asp Tyr Thr Arg His Phe Leu Ser Ala Cys Ser
        210                 215                 220

Arg Leu Leu Gly Leu Thr Thr Thr Pro Asn Gly Ile Glu Phe Gln Gly
225                 230                 235                 240

Lys Ile Ile Ala Cys Gly Ala Phe Pro Ile Gly Ile Asp Pro Glu Lys
                245                 250                 255

Phe Glu Glu Gly Leu Lys Lys Glu Lys Val Gln Lys Arg Ile Ala Met
            260                 265                 270

Leu Glu Gln Lys Phe Gln Gly Val Lys Leu Met Val Gly Val Asp Arg
        275                 280                 285

Leu Asp Tyr Ile Lys Gly Val Pro Gln Lys Leu His Ala Leu Glu Val
        290                 295                 300

Phe Leu Ser Asp His Pro Glu Trp Val Gly Lys Val Val Leu Val Gln
305                 310                 315                 320

Val Ala Val Pro Ser Arg Gln Asp Val Glu Glu Tyr Gln Asn Leu Arg
                325                 330                 335

Ala Val Val Asn Glu Leu Val Gly Arg Ile Asn Gly Lys Phe Gly Thr
            340                 345                 350

Val Glu Phe Met Pro Ile His Phe Leu His Lys Ser Val Asn Phe Asp
        355                 360                 365
```

-continued

```
Glu Leu Ile Ala Leu Tyr Ala Val Ser Asp Ala Cys Ile Val Ser Ser
    370                 375                 380

Thr Arg Asp Gly Met Asn Leu Val Ala Tyr Glu Tyr Ile Ala Thr Gln
385                 390                 395                 400

Lys Lys Arg His Gly Val Leu Val Leu Ser Glu Phe Ala Gly Ala Ala
                405                 410                 415

Gln Ser Leu Asn Gly Ser Ile Ile Ile Asn Pro Trp Asn Thr Glu Glu
                420                 425                 430

Leu Ala Gly Ala Tyr Gly Glu Ala Val Thr Met Ser Asp Glu Gln Arg
                435                 440                 445

Ala Leu Asn Phe Ser Lys Leu Asp Lys Tyr Val Asn Lys Tyr Thr Ser
                450                 455                 460

Ala Phe Trp Gly Gln Ser Phe Val Thr Glu Leu Thr Arg Ile Ser Glu
465                 470                 475                 480

His Ser Ala Glu Lys Phe His Ala Lys Lys Ala Ser Phe Ser Asp Asn
                485                 490                 495

Asn Ser Glu Asn Gly Glu Pro Ser Asn Gly Val Glu Thr Pro Ala Gln
                500                 505                 510

Glu Gln Val Ala Gln
        515
```

(2) INFORMATION FOR SEQ ID NO:4:

(i) SEQUENCE CHARACTERISTICS:
        (A) LENGTH: 479 amino acids
        (B) TYPE: amino acid
        (C) STRANDEDNESS: single
        (D) TOPOLOGY: linear (xi) SEQUENCE DESCRIPTION: SEQ ID NO:4:

```
Met Ser Asp Ala His Asp Thr Ile Lys Ser Leu Thr Gly Asp Ala Ser
1               5                   10                  15

Asn Ser Arg Arg Leu Ile Val Val Ser Asn Arg Leu Pro Ile Thr Ile
                20                  25                  30

Lys Arg Lys Asp Asn Gly Thr Tyr Asp Phe Ser Met Ser Ser Gly Gly
                35                  40                  45

Leu Val Ser Ala Leu Ser Gly Leu Lys Lys Leu Met Thr Phe Gln Trp
    50                  55                  60

Leu Gly Trp Cys Gly Gln Glu Ile Pro Glu Asp Glu Lys Pro Met Ile
65              70                  75                  80

Ile Gln Arg Leu Gln Asp Glu Cys Ser Ala Ile Pro Val Phe Leu Asp
                85                  90                  95

Asp Glu Thr Ala Asp Arg His Tyr Asn Gly Phe Ser Asn Ser Ile Leu
                100                 105                 110

Trp Pro Leu Phe His Tyr His Pro Gly Glu Ile Asn Phe Asp Glu Glu
                115                 120                 125

Asn Trp Glu Ala Tyr Arg Ala Ala Asn Tyr Ala Phe Ala Glu Ala Ile
                130                 135                 140

Val Lys Asn Leu Gln Asp Gly Asp Leu Ile Trp Val Gln Asp Val His
145                 150                 155                 160

Leu Met Val Leu Pro Gln Met Leu Arg Glu Leu Ile Gly Asp Lys Phe
                165                 170                 175

Lys Asp Ile Lys Ile Gly Phe Phe Leu His Thr Pro Phe Pro Ser Ser
                180                 185                 190

Glu Ile Tyr Arg Val Leu Pro Val Arg Asn Glu Ile Leu Glu Gly Val
                195                 200                 205
```

—continued

```
Leu Asn Cys Asp Leu Val Gly Phe His Thr Tyr Asp Tyr Ala Arg His
    210                 215                 220
Phe Leu Ser Ala Cys Ser Arg Ile Leu Asn Leu Ser Thr Leu Pro Asn
225                 230                 235                 240
Gly Val Glu Tyr Asn Gly Gln Met Val Ser Val Gly Thr Phe Pro Ile
            245                 250                 255
Gly Ile Asp Pro Glu Lys Phe Ser Asp Ala Leu Lys Ser Asp Val Val
                260                 265                 270
Lys Asp Arg Ile Arg Ser Ile Glu Arg Leu Gln Gly Val Lys Val
            275                 280                 285
Ile Val Gly Val Asp Arg Leu Asp Tyr Ile Lys Gly Val Pro Gln Lys
    290                 295                 300
Phe His Ala Phe Glu Val Phe Leu Glu Gln Tyr Pro Glu Trp Val Gly
305                 310                 315                 320
Lys Val Val Leu Val Gln Val Ala Val Pro Ser Arg Gln Asp Val Glu
            325                 330                 335
Glu Tyr Gln Asn Leu Arg Ala Val Val Asn Glu Leu Val Gly Arg Ile
                340                 345                 350
Asn Gly Arg Phe Gly Thr Val Glu Tyr Thr Pro Ile His Phe Leu His
            355                 360                 365
Lys Ser Val Arg Phe Glu Glu Leu Val Ala Leu Tyr Asn Val Ser Asp
    370                 375                 380
Val Cys Leu Ile Thr Ser Thr Arg Asp Gly Met Asn Leu Val Ser Tyr
385                 390                 395                 400
Glu Tyr Ile Cys Thr Gln Gln Glu Arg His Gly Ala Leu Ile Leu Ser
            405                 410                 415
Glu Phe Ala Gly Ala Ala Gln Ser Leu Asn Gly Ser Ile Val Ile Asn
                420                 425                 430
Pro Trp Asn Thr Glu Glu Leu Ala Asn Ser Ile His Asp Ala Leu Thr
            435                 440                 445
Met Pro Glu Lys Gln Arg Glu Ala Asn Glu Asn Lys Leu Phe Arg Tyr
    450                 455                 460
Val Asn Lys Tyr Thr Ser Gln Phe Trp Gly Pro Lys Leu Cys Arg
465                 470                 475
```

(2) INFORMATION FOR SEQ ID NO:5:

(i) SEQUENCE CHARACTERISTICS:
        (A) LENGTH: 498 amino acids
        (B) TYPE: amino acid
        (C) STRANDEDNESS: single
        (D) TOPOLOGY: linear (xi) SEQUENCE DESCRIPTION: SEQ ID NO:5:

```
Met Thr Ser Arg Gly Asn His Gly Ser Lys Thr Ser Ser Asp Lys His
1               5                   10                  15
Leu Gly Asp Ser Asp Phe Val Val Ala Asn Arg Leu Pro Val Asp
            20                  25                  30
Gln Val Arg Leu Pro Asp Gly Thr Ala Ile Trp Lys Arg Ser Pro Gly
                35                  40                  45
Gly Leu Val Thr Ala Leu Glu Pro Leu Leu Arg Gln Arg Arg Gly Ala
        50                  55                  60
Trp Val Gly Trp Pro Gly Val Ile Asn Asp Asn Val Asp Leu Asp Leu
65                  70                  75                  80
Thr Ile Lys Ser Ile Val Gln Asp Gly Leu Thr Leu Tyr Pro Val Arg
```

-continued

```
                    85                  90                  95
Leu Asn Thr His Asp Val Ala Glu Tyr Tyr Glu Gly Phe Ser Asn Ala
                100                 105                 110
Thr Leu Trp Pro Leu Tyr His Asp Val Ile Val Lys Pro Ile Tyr His
            115                 120                 125
Cys Glu Trp Trp Glu Arg Tyr Val Asp Val Asn Arg Arg Phe Ala Glu
        130                 135                 140
Thr Thr Ser Arg Thr Ala Ala Tyr Gly Gly Thr Val Trp Val Gln Asp
145                 150                 155                 160
Tyr Gln Leu Gln Leu Val Pro Lys Met Leu Arg Ile Met Arg Pro Asp
                165                 170                 175
Leu Thr Ile Gly Phe Phe Leu His Ile Pro Phe Pro Pro Val Glu Leu
            180                 185                 190
Phe Met Gln Ile Pro Trp Arg Thr Glu Ile Ile Glu Gly Leu Leu Gly
        195                 200                 205
Ala Asp Leu Val Gly Phe His Leu Thr Ser Gly Ala Gln Asn Phe Leu
    210                 215                 220
Phe Leu Ser Arg His Leu Leu Gly Ala Asn Thr Ser Arg Gly Leu Val
225                 230                 235                 240
Gly Val Arg Ser Arg Phe Gly Glu Val Gln Leu Lys Ser His Thr Val
                245                 250                 255
Gln Val Gly Ala Phe Pro Ile Ser Ile Asp Ser Lys Glu Ile Asp Gln
            260                 265                 270
Ala Thr Arg Asp Arg Asn Val Arg Arg Ala Arg Glu Ile Arg Ala
        275                 280                 285
Glu Leu Gly Asn Pro Arg Lys Ile Leu Leu Gly Val Asp Arg Leu Asp
    290                 295                 300
Tyr Thr Lys Gly Ile Asp Val Arg Leu Arg Ala Phe Ala Glu Leu Leu
305                 310                 315                 320
Ala Glu Gly Arg Ala Lys Arg Asp Asp Thr Val Leu Val Gln Leu Ala
                325                 330                 335
Thr Pro Ser Arg Glu Arg Val Glu Ser Tyr Lys Ile Leu Arg Asn Asp
            340                 345                 350
Ile Glu Arg Gln Val Gly His Ile Asn Gly Glu Tyr Gly Glu Val Gly
        355                 360                 365
His Pro Val Val His Tyr Leu His Arg Pro Ile Pro Arg Asp Glu Leu
    370                 375                 380
Ile Ala Phe Tyr Val Ala Ser Asp Val Met Leu Val Thr Pro Leu Arg
385                 390                 395                 400
Asp Gly Met Asn Leu Val Ala Lys Glu Tyr Val Ala Cys Arg Asn Asp
                405                 410                 415
Leu Gly Gly Ala Leu Val Leu Ser Glu Phe Thr Gly Ala Ala Ala Glu
            420                 425                 430
Leu Arg Gln Ala Tyr Leu Val Asn Pro His Asp Leu Glu Gly Val Lys
        435                 440                 445
Asp Thr Ile Glu Ala Ala Leu Asn Gln Leu Ala Glu Ala Arg Arg
    450                 455                 460
Arg Met Arg Ser Leu Arg Arg Gln Val Leu Ala His Asp Val Asp Arg
465                 470                 475                 480
Trp Ala Arg Ser Phe Leu Asp Ala Leu Ala Glu Ala Pro Ala Arg Asp
                485                 490                 495
Ala Thr
```

(2) INFORMATION FOR SEQ ID NO:6:

(i) SEQUENCE CHARACTERISTICS:
        (A) LENGTH: 473 amino acids
        (B) TYPE: amino acid
        (C) STRANDEDNESS: single
        (D) TOPOLOGY: linear (xi) SEQUENCE DESCRIPTION: SEQ ID NO:6:

```
Ser Arg Leu Val Val Ser Asn Arg Ile Ala Pro Pro Asp Glu His
 1               5                  10                  15

Ala Ala Ser Ala Gly Gly Leu Ala Val Gly Ile Leu Gly Ala Leu Lys
            20                  25                  30

Ala Ala Gly Gly Leu Trp Phe Gly Trp Ser Gly Glu Thr Gly Asn Glu
        35                  40                  45

Asp Gln Pro Leu Lys Lys Val Lys Lys Gly Asn Ile Thr Trp Ala Ser
    50                  55                  60

Phe Asn Leu Ser Glu Gln Asp Leu Asp Glu Tyr Tyr Asn Gln Phe Ser
65                  70                  75                  80

Asn Ala Val Leu Trp Pro Ala Phe His Tyr Arg Leu Asp Leu Val Gln
                85                  90                  95

Phe Gln Arg Pro Ala Trp Asp Gly Tyr Leu Arg Val Asn Ala Leu Leu
            100                 105                 110

Ala Asp Lys Leu Leu Pro Leu Leu Gln Asp Asp Ile Ile Trp Ile
        115                 120                 125

His Asp Tyr His Leu Leu Pro Phe Ala His Glu Leu Arg Lys Arg Gly
    130                 135                 140

Val Asn Asn Arg Ile Gly Phe Phe Leu His Ile Pro Phe Pro Thr Pro
145                 150                 155                 160

Glu Ile Phe Asn Ala Leu Pro Thr Tyr Asp Thr Leu Leu Glu Gln Leu
                165                 170                 175

Cys Asp Tyr Asp Leu Leu Gly Phe Gln Thr Glu Asn Asp Arg Leu Ala
            180                 185                 190

Phe Leu Asp Cys Leu Ser Asn Leu Thr Arg Val Thr Thr Arg Ser Ala
        195                 200                 205

Lys Ser His Thr Ala Trp Gly Lys Ala Phe Arg Thr Glu Val Tyr Pro
    210                 215                 220

Ile Gly Ile Glu Pro Lys Glu Ile Ala Lys Gln Ala Ala Gly Pro Leu
225                 230                 235                 240

Pro Pro Lys Leu Ala Gln Leu Lys Ala Glu Leu Lys Asn Val Gln Asn
                245                 250                 255

Ile Phe Ser Val Glu Arg Leu Asp Tyr Ser Lys Gly Leu Pro Glu Arg
            260                 265                 270

Phe Leu Ala Tyr Glu Ala Leu Leu Glu Lys Tyr Pro Gln His His Gly
        275                 280                 285

Lys Ile Arg Tyr Thr Gln Ile Ala Pro Thr Ser Arg Gly Asp Val Gln
    290                 295                 300

Ala Tyr Gln Asp Ile Arg His Gln Leu Glu Asn Glu Ala Gly Arg Ile
305                 310                 315                 320

Asn Gly Lys Tyr Gly Gln Leu Gly Trp Thr Pro Leu Tyr Tyr Leu Asn
                325                 330                 335

Gln His Phe Asp Arg Lys Leu Leu Met Lys Ile Phe Arg Tyr Ser Asp
            340                 345                 350

Val Gly Leu Val Thr Pro Leu Arg Asp Gly Met Asn Leu Val Ala Lys
        355                 360                 365
```

```
Glu Tyr Val Ala Ala Gln Asp Pro Ala Asn Pro Gly Val Leu Val Leu
    370             375             380

Ser Gln Phe Ala Gly Ala Ala Asn Glu Leu Thr Ser Ala Leu Ile Val
385         390             395                 400

Asn Pro Tyr Asp Arg Asp Glu Val Ala Ala Ala Leu Asp Arg Ala Leu
            405             410             415

Thr Met Ser Leu Ala Glu Arg Ile Ser Arg His Ala Glu Met Leu Asp
            420             425             430

Val Ile Val Lys Asn Asp Ile Asn His Trp Gln Glu Cys Phe Ile Ser
        435             440             445

Asp Leu Lys Gln Ile Val Pro Arg Ser Ala Glu Ser Gln Gln Arg Asp
    450             455             460

Lys Val Ala Thr Phe Pro Lys Leu Ala
465             470
```

METHODS OF PRESERVING PROKARYOTIC CELLS AND COMPOSITIONS OBTAINED THEREBY

RELATED APPLICATIONS

This application claims the priority benefit of U.S. Provisional Application Serial No. 60/032,423 and its filing date of Dec. 5, 1996.

TECHNICAL FIELD

This invention relates to the field of preserving cells. More specifically, it relates to methods of drying and stabilizing prokaryotic cells and the compositions obtained thereby.

BACKGROUND ART

Live prokaryotic cells, particularly bacteria, are widely and increasingly used in important medical, agricultural and industrial applications. Agricultural, or environmental, applications include biopesticides and bioremediation. Medical applications include use of live bacteria in vaccines as well as production of pharmaceutical products and numerous industrial compositions. The use of live bacterial vaccines promises only to increase, given the dramatic rise in biotechnology as well as the intensive research into the treatment of infectious diseases over the past twenty years.

Bacterial cells must be able to be stored for significant periods of time while preserving their viability to be used effectively both in terms of desired results and cost. Storage viability has proven to be a major difficulty. Methods for preserving live prokaryotic cells suffer from several serious drawbacks, such as being energy-intensive and requiring cold storage. Furthermore, existing preservation methods fail to provide satisfactory viability upon storage, especially if cells are stored at ambient or higher temperature.

Freeze-drying is often used for preservation and storage of prokaryotic cells. However, it has the undesirable characteristics of significantly reducing viability as well as being time- and energy-intensive and thus expensive. Freeze-drying involves placing the cells in solution, freezing the solution, and exposing the frozen solid to a vacuum under conditions where it remains solid and the water and any other volatile components are removed by sublimation. The resulting dried formulation comprises the prokaryotic cells.

In spite of the apparent ubiquity of freeze-drying, freeze-dried bacteria are unstable at ambient temperatures, thus necessitating storage by refrigeration. Even when refrigerated, however, the cells can quickly lose viability. Damage caused by this process may be circumvented, to a certain degree, by the use of excipients such as lyoprotectants. However, lyoprotectants may subsequently react with the dried cells, imposing inherent instability upon storage of the freeze-dried prokaryotic cells.

Other methods used to prepare dry, purportedly stable preparations of prokaryotic cells such as ambient temperature drying, spray drying, liquid formulations, and freezing of bacterial cultures with cryoprotectants also have drawbacks. For a general review on desiccation tolerance of prokaryotes, see Potts (1994) *Micro. Rev.* 58:755–805. Ambient temperature drying techniques eliminate the freezing step and associated freeze-damage to the substance, and these techniques are more rapid and energy-efficient in the removal of water. Crowe et al. (1990) *Cryobiol.* 27:219–231. However, ambient temperature drying often yields unsatisfactory viability. Spray drying results in limited storage time and reduced viability, even when stabilizing excipients are used. For a general review, see Lievense and van't Reit (1994) *Adv. Biochem. Eng. Biotechnol.* 51 :45–63; 72–89. Liquid formulations may provide only short-term stabilization and require refrigeration. Freezing bacterial cultures results in substantial damage to the bacterial cell wall and loss of viability which is only reduced but not eliminated by the use of cryoprotectants. Moreover, these frozen cultures also need to be stored refrigerated.

Trehalose, ($\alpha$-D-glucopyranosyl-$\alpha$-D-glucopyranoside), is a naturally occurring, non-reducing disaccharide which was initially found to be associated with the prevention of desiccation damage in certain plants and animals which can dry out without damage and can revive when rehydrated. Trehalose has been shown to be useful in preventing denaturation of proteins, viruses and foodstuffs during desiccation. See U.S. Pat. Nos. 4,891,319; 5,149,653; 5,026,566; Blakeley et al. (1990) *Lancet* 336:854–855; Roser (July 1991) *Trends in Food Sci. and Tech.* 10:166–169; Colaco et al. (1992) *Biotechnol. Internat.* 1:345–350; Roser (1991) *BioPharm.* 4:47–53; Colaco et al. (1992) *Bio/Tech.* 10:1007–1011; and Roser et al. (May 1993) *New Scientist*, pp. 25–28. Trehalose dihydrate is available commercially in good manufacturing process (GMP) grade crystalline formulations. A method of making trehalose from starch is described in EP patent publication No. 639 645 A1. This method involves a two step enzymatic bioconversion of starch to yield a trehalose syrup from which the sugar is recovered by crystallisation.

Bacteria are able to counteract osmotic shock by accumulating and/or synthesizing potassium with a few types of organic molecules, including some sugars. Osmoregulation in bacteria such as *Escherichia coli* in glucose-mineral medium without any osmoprotective compounds involves the endogenous production of trehalose. Larsen et al. (1987) *Arch. Microbiol.* 147:1–7; Dinnbier et al. (1988) *Arch. Microbiol.* 150:348–357; Giaever et al. (1988) *J. Bacteriol.* 170:2841–2849; and Welsh et al. (1991) *J. Gen. Microbiol.* 137:745–750.

One method of preserving prokaryotic cells is freeze-drying in the presence of trehalose. See, e.g., Israeli et al. (1993) *Cryobiol.* 30:519–523. However, this method provides unsatisfactory viability. Israeli et al. freeze dried *E. coli* in the presence of 100 mM trehalose but reported survival data for only four days after exposure of the dried samples to air at 21° C. A later study tested survival rates of *E. coli* and *Bacillus fluoringiensis* freeze-dried in the presence of trehalose. Leslie et al. (1995) *Appl. Env. Microbiol.* 61:3592–3597. Survival data were reported only for 4 days after exposure of the dried samples to air.

Another study comparing freeze-dried to air-dried (sealed under nitrogen) *E. coli* in the presence of trehalose reported survival rates of about $10^7$ to over $10^{10}$ colony forming units (CFU) per ml for cells stored for 25 weeks, but the cells were stored at 4° C. Louis et al. (1994) *Appl. Microbiol. Biotechnol.* 41:684–688.

In view of increasing applications for viable bacteria and the existing problems regarding maintaining bacterial viability during storage, there is a pressing need for a method to inexpensively dry and stabilize prokaryotic cells. It is especially desirable to develop methods that would allow storage of dried prokaryotic cells at ambient temperature, i.e., not requiring refrigeration. The methods described herein address this need by providing dry, remarkably storage-stable, prokaryotic cells that retain viability without the need for refrigeration.

All references cited herein are hereby incorporated herein by reference in their entirety.

SUMMARY OF THE INVENTION

The present invention encompasses methods of producing dried, stabilized prokaryotic cells. The invention also includes compositions produced by these methods, as well as methods of reconstituting the prokaryotic cells.

A more detailed description of this assay is provided in Example 2. Preferably, residual moisture will be equal to or less than about 5%, more preferably less than about 4%, more preferably equal to or less than about 3% even more preferably equal to or less than about 2.5%. When cells are dried more rapidly by gradually increasing the temperature, as described above, residual moisture may drop below 2%. The allowable maximum for different cell types can easily be determined empirically. Generally, residual moisture above about 5% can be detrimental to viability. This varies depending, inter alia, on the genus/species/strain used, the concentration and type of non-reducing carbohydrate used in the drying solution, method of drying and type of storage.

BRIEF DESCRIPTION OF THE DRAWINGS

FIG. 1 shows the alignment of trehalose synthase amino acid sequences encoded by genes from a variety of organisms: 1. *Kluyveromyces lactis*; 2. *Saccharomyces cerevisiae*; 3. *Aspergillus niger*; 4. *Schizosaccharomyces pombe*; 5. *Mycobacterium leprae*; and 6. *E. coli* (SEQ ID NOS: 1–6, respectively).

FIG. 2 is a half-tone reproduction of a Southern blot testing for the presence of trehalose synthase genes in *E. coli* and Salmonella. The horizontal lines on the left represent molecular weight markers (λ Hind III) of 23, 9.3, 6.6, 4.4, 2.3, 2.0 and 0.56 kb, respectively.

FIG. 6A shows the accumulation of intracellular trehalose concentration and growth curve for *E. coli* grown at 37° C. in Evans medium and 0.5 M NaCl. FIG. 6B shows accumulation of intracellular trehalose concentration and growth curve at 37° C. for *E. coli* grown at 37° C. in Evans medium lacking NaCl. In both A and B, the circles represent induced trehalose concentration and the squares represent cell growth (absorbance) measured at 600 nm.

MODES FOR CARRYING OUT THE INVENTION

Figure 3:
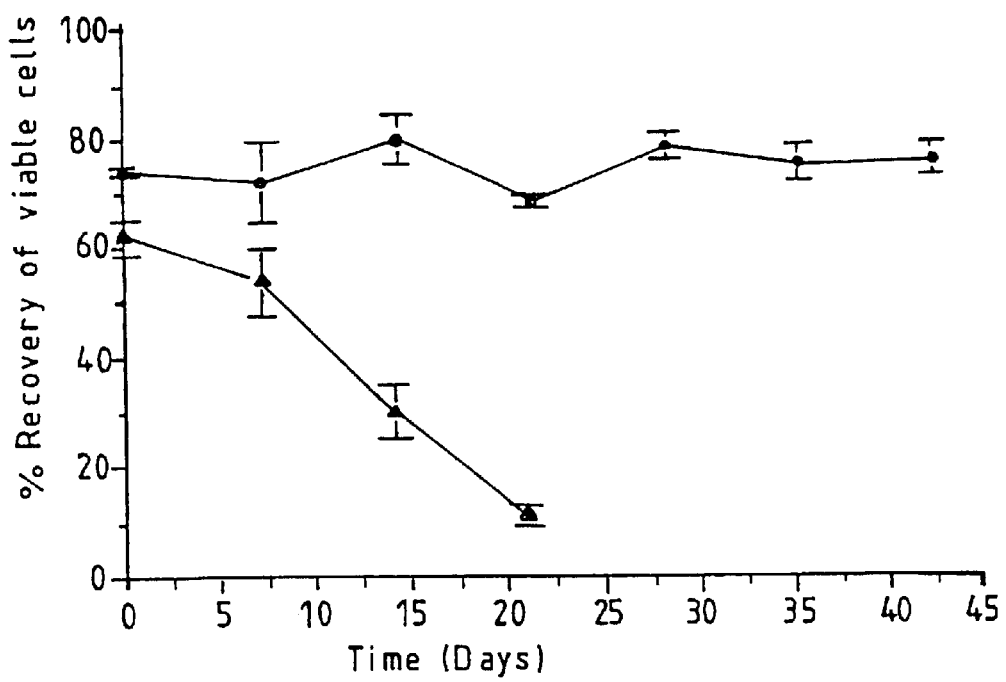
FIG. 3 is a graph depicting stability of *E. coli* NCIMB 9484 after storage at 37° C. The circles indicate intracellular trehalose induction and the triangles represent no trehalose induction.

We have found that prokaryotic cells can be dried and stabilized by inducing intracellular trehalose production to an amount effective to increase storage stability and drying the cells in the presence of a stabilizing agent. The methods for stabilizing prokaryotic cells described herein can be used for producing dried, stable bacteria useful for pharmacological treatment, prophylaxis, agricultural and industrial applications.

Prokaryotic cells obtained by the methods disclosed herein are remarkably stable: bacteria stabilized by these methods retain high viability even after storage at ambient or above ambient temperatures. Bacteria dried under these conditions retain about 50–80% viability upon drying. Furthermore, bacteria stabilized by these methods show less than 10% loss of viability on storage even after being stored at temperatures up to at least 37° C. for as long as six weeks. This degree of stabilization during drying and storage is significantly greater than previously reported using other methods. The stabilized cells can be stored at room temperature and thus do not require refrigeration. Depending on the conditions, drying can generally be accomplished within 24 hours which provides energy and cost savings as well as increased viability.

The methods and compositions of the invention facilitate the development of many needed, useful products, including, but not limited to: (i) live bacterial vaccines in a dry stable form; (ii) live bacterial neutraceuticals in a dry stable form; (iii) other live bacterial pharmaceutical products in a dry stable form, e.g., for treatment of vaginal or urinary tract infections; (iv) live bacterial starter cultures in a dry stable form for commercial products such as for the dairy industry; (v) live bacteria in a dry stable form for agricultural, ecological or bioremedial use, such as pesticides; and (vi) live bacterial cultures in a dry stable form for the biotechnology industry.

As used herein, "prokaryotic cells" are cells that exhibit characteristics of prokaryotes, which is a term well known in the art. Prokaryotes are typically unicellular organisms and lack organelles (such as mitochondria, chloroplasts, and Golgi apparatus), a cytoskeleton, and a discrete nucleus. Examples of prokaryotic cells include bacteria, such as eubacteria, cyanobacteria and prochlorophytes; archaebacteria; and other microorganisms such as rickettsias, mycoplasmas, spiroplasmas, and chlamydiae. For purposes of this invention, prokaryotes are capable of synthesizing trehalose. This ability can be native or conferred by recombinant techniques. The ability to synthesize trehalose can be determined by measuring intracellular trehalose concentration, which is described below. Preferably, the prokaryotic cells are bacteria. Examples of bacteria include, but are not limited to, Escherichia, Bacillus(including Lactobacillus), Salmonella, and Vibrio.

The stabilizing agents are preferably carbohydrates. "Carbohydrates" include, but are not limited to, monosaccharides, disaccharides, trisaccharides, oligosaccharides and their corresponding sugar alcohols, polyhydroxyl compounds such as carbohydrate derivatives and chemically modified carbohydrates, hydroxyethyl starch and sugar copolymers. Both natural and synthetic carbohydrates are suitable for use herein. Synthetic carbohydrates include, but are not limited to, those which have the glycosidic bond replaced by a thiol or carbon bond. Both D and L forms of the carbohydrates may be used. For purposes of this invention, the carbohydrate is preferably non-reducing. Preferably, the non-reducing carbohydrate is trehalose. Other examples of preferred non-reducing carbohydrates are provided below.

Conditions that "increase intracellular trehalose concentration" are conditions that initiate, encourage, allow, and/or increase the rate of synthesis of trehalose within the cell(s), and/or increase the amount of trehalose within the cell(s) when compared to growing or incubating the cell(s) without these conditions. Conditions (including preferred conditions) that stimulate production of intracellular production of trehalose are discussed in detail below. Examples of these conditions include, but are not limited to, growing the cell(s) under stressful conditions such as osmotic shock, i.e., high salt conditions. Conditions that stimulate production of intracellular trehalose can also be effected by, for example, inhibiting the rate of degradation of trehalose, expressing recombinant genes and inducing uptake of exogenous trehalose.

"Ambient" is a term of art referring to the atmospheric pressure or humidity or temperature of the room in which the methods described are being performed. Ambient temperature is also referred to as room temperature and is generally from about 15–25° C.

"Residual moisture" is the amount of water remaining (expressed in weight percent) after drying prokaryotic cells by the methods described herein. Residual moisture can be measured by Karl/Fischer Coulometer, as discussed in more detail below.

"Glass" is a term well understood in the art, especially as applied to carbohydrate glasses. For purposes of this invention, "glass" refers to a non-crystalline, vitreous, solid physical state achieved upon sufficient loss of water.

As used herein, "foamed glass matrix" (FGM) refers to a carbohydrate-containing glass that contains bubbles dispersed in the glass, resulting in a foam. For purposes of this invention, a foamed glass matrix contains less than about 5% residual moisture, preferably less than about 4% residual moisture, more preferably less than about 2% residual moisture.

"High osmolarity" refers to excessive solute concentration in growth media. "Excessive" solute concentration means that solute concentration (generally salts) is above the level at which a cell exists and/or grows in its native environment.

"Viability" is a term well understood in the art, and is consonantly used herein to mean manifestations of a functioning living organism, such as metabolism and cell division. Methods to measure viability are known in the art and are described herein.

The present invention encompasses methods of producing stabilized prokaryotic cells and the cells produced thereby. These methods comprise the steps of increasing intracellular trehalose, preferably by culturing or incubating the prokaryotic cells under conditions that increase intracellular trehalose concentration to an amount effective to increase storage stability; mixing the prokaryotic cells with a drying solution which contains a stabilizing agent, preferably a non-reducing carbohydrate such as trehalose; and drying the resulting mixture such that a glass is produced having less than about 5% residual moisture.

Growing prokaryotic cells to increase intracellular trehalose concentration. To practice the methods of this invention, prokaryotic cells can be grown under conditions that increase intracellular trehalose concentration. Intracellular trehalose can be measured using standard methods in the art as described below. Any prokaryotic cell, particularly bacteria, containing trehalose synthase genes, whether endogenous or recombinant, should be capable of producing intracellular trehalose.

Many types of prokaryotic cells are known to synthesize trehalose. Examples of bacteria that contain the trehalose synthase gene include, but are not limited to, Enterobacteriaceae, such as Salmonella and Escherichia (e.g., *S. typhimurium* and *E. coli*); halophilic and halotolerant bacteria, such as Ectothriorhodospira (e.g., *E. halochloris*); micrococcocaceae, such as Micrococcus (e.g., *M luteus*); Rhizobium species such as *R. japonicum* and *R. leguminosarum bv phaseoli*; Cyanobacteria and Mycobacteria species such as *M. tuberculosis, M. bovis,* and *M. smegmatis*. An alignment of trehalose synthases encoded by genes from a variety of organisms is shown in FIG. 1. Several other bacteria have been shown to have trehalose synthase genes all of which are highly homologous to the *E. coli* gene. These bacteria include *Pseudomonas putidae* and *Aeromonas salmonicida*.

Determining whether a particular bacteria species contains trehalose synthase gene(s) can be accomplished by, for example, searching available nucleic acid (and/or protein) databases for the presence of sequences that encode (or that correspond to) consensus regions of the amino acid sequence for trehalose synthase genes. Bacteria have two genes involved in trehalose synthesis (i.e., T-Phosphate synthase and T-6-P phosphatase), whereas yeast have at least three genes. Generally, searching with probes specific for the yeast genes also identifies the bacterial genes, albeit with lower homology scores. Amino acid sequence alignments of trehalose synthase show homology between bacteria, yeast and fungi and more specific search and screening probes can be determined from these alignments (FIG. 1). Alternatively, Southern blots can be produced of genomic DNA from a test cell probed with DNA encoding all or a functional portion of a trehalose synthase gene. FIG. 2 shows a Southern blot of the trehalose synthase genes of *E. coli*, and two strains of Salmonella. Alternatively, PCR-based detection can be used. These methods are well-known in the art.

Increases in intracellular trehalose can be obtained by culturing the cells under stressful conditions, e.g., osmotic shock, heat or oxygen limitation (shock), carbon/nitrogen starvation, or any combination of the above. Alternatively, use of inhibitors of enzyme(s) involved in trehalose degradation (i.e., trehalase), such as validomycin, also results in accumulation of intracellular trehalose. Suitable conditions can be determined empirically and are well within the skill of one in the art. While not wishing to be bound to a particular theory, induction of trehalose production under stressful conditions may trigger synthesis or accumulation of other molecules beneficial for preservation, such as betaine and chaperoning.

For bacteria, particularly Escherichia, trehalose production can be stimulated by growing the cell(s) in conditions of high osmolarity, i.e., solute (generally salt) concentrations sufficient to stimulate trehalose production. Thus, the invention encompasses culturing prokaryotic cells in osmolarity of at least about 350 mOsmoles to about 1.5 Osmoles, preferably at least about 400 mOsmoles to 1 Osmole, more preferably 250 mOsmoles to 500 mOsmoles. The invention also encompasses culturing prokaryotic cells in osmolarity of at least about 300 mOsmoles, preferably at least about 400 mOsmoles, more preferably at least about 500 mOsmoles. Generally, a minimum salt concentration of about 200 mOsmoles is required but an effective concentration can be derived empirically. A single salt can be sufficient to stimulate trehalose production, for example, 200 mM NaCl. KCl and $CaCl_2$ also stimulate intracellular trehalose production, indicating that intracellular trehalose production is not dependent on the action used or the concentration of chloride in the growth medium. When $(NH_4)_2SO_4$ is used, however, only about one half of the amount of trehalose is produced compared to that produced in the presence of KCl, NaCl and $CaCl_2$. A combination of salts can also be used. In addition, when used to increase the osmolarity of the medium, a non-penetrant solute such as sorbitol and/or glucose can contribute to the stimulation of trehalose accumulation.

Examples of salts that can be used to increase the osmolarity include, but are not limited to, sodium phosphate ($Na_2PO_4$); potassium phosphate ($KH_2PO_4$); ammonium chloride ($NH_4Cl$); sodium chloride (NaCl); magnesium sulfate ($MgSO_4$); calcium chloride ($CaCl_2$); thiamine hydrochloride or any combination thereof. In a preferred embodiment, minimal medium contains about 0.5 M salt. Even more preferably, the 0.5 M salt is composed of the following: $Na_2HPO_4$, 6 g/l; $KH_2PO_4$, 3 g/l; $NH_4Cl$, 0.267 g/l; NaCl, 29.22 g/l; 1 M $MgSO_4$, 1 ml/l; 0.1 M $CaCl_2$ (1 ml/l); thiamine HCl, 1 ml/l; with glucose at final concentration of 2.5% w/v. Sufficient glucose should be available for a carbon source and trehalose production. Determining sufficient glucose concentrations can be determined empirically and is well within the skill of one in the art.

The salt concentration (i.e., osmolarity) required to stimulate and/or induce trehalose production will depend upon the genus, species, and/or strain of the prokaryotic cell used. Preferably, cell(s) are grown in a minimal medium containing salt. Commercially available minimal medium is supplemented with desired salts and/or other solutes, although minimal medium is not essential and defined media can also be used. The time required to initiate and achieve the desired level of intracellular trehalose concentration will vary depending on the level of osmolarity as well as the genus, species and/or strain of prokaryotic cell used and can be determined empirically. Trehalose synthesis will generally begin within an hour of placing cells in conditions designed to stimulate trehalose production. Generally, in E. coli the amount of intracellular trehalose reaches a maximum at about 15 to 20 hours after placing cells in conditions that stimulate trehalose production.

To induce intracellular trehalose production by osmotic shock, the total concentration of salt(s) in the medium should be at least about 0.2 M, preferably at least about 0.4 M, more preferably at least about 0.5 M. In the case of E. coli, the total concentration of salt(s) should not exceed 0.6 M. At about 0.6 M or above, intracellular trehalose production declines in E. coli. The salt concentration required for the desired result may vary depending on the general/species/strain used, and can be determined empirically.

Intracellular trehalose can also be increased using recombinant methods which are well known in the art. For instance, prokaryotic cells can be transfected with a DNA plasmid comprising a DNA sequence encoding an appropriate trehalose synthase gene. Suitable genes are available from a wide variety of resources as indicated by the number of genes depicted in FIG. 1 and other genes recently identified. The gene in turn is operatively linked to a suitable promoter, which can be constitutive or inducible. Recombinant methods are described in a variety of references, such as "Molecular Cloning: A Laboratory Manual," second edition (Sambrook et al., 1989).

Intracellular trehalose can be measured by using assays known in the art, such as by high pressure liquid chromotography (HPLC), coupled with electro-chemical detection and glucose assay (Trinder assay using trehalase) for quantitative enzymatic determination of trehalose. Thin layer chromatography can be used as a qualitative method for the separation of different carbohydrates. Refractive index detection provides another means of detecting sugars quantitatively.

In measuring trehalose by HPLC, cells are disrupted and intracellular trehalose preferentially solubilized in 70% ethanol, followed by removing triglycerides by chloroform extraction. Intracellular trehalose concentration is determined by multiplying trehalose concentration (as determined by a standard curve) by the fraction of final volume of supernatant divided by pellet volume. A more detailed description of this assay is provided in Example 1.

Preferably, the concentration of intracellular trehalose is at least about 50 mM; more preferably, at least about 100 mM; more preferably, at least about 150 mM; more preferably, at least about 200 mM; more preferably, at least about 250 mM; and even more preferably, at least about 300 mM. We have found that stability of bacteria decreases markedly using the methods described herein if the intracellular trehalose concentration is below about 30 mM. Thus, the invention encompasses culturing the prokaryotic cells under conditions that stimulate intracellular production of trehalose, wherein intracellular concentration of trehalose reaches at least about 30 mM, preferably at least about 50 mM, preferably at least about 100 mM, more preferably at least about 150 mM, more preferably at least about 200 mM, more preferably at least about 250 mM, and even more preferably at least about 300 mM.

Figure 6A:
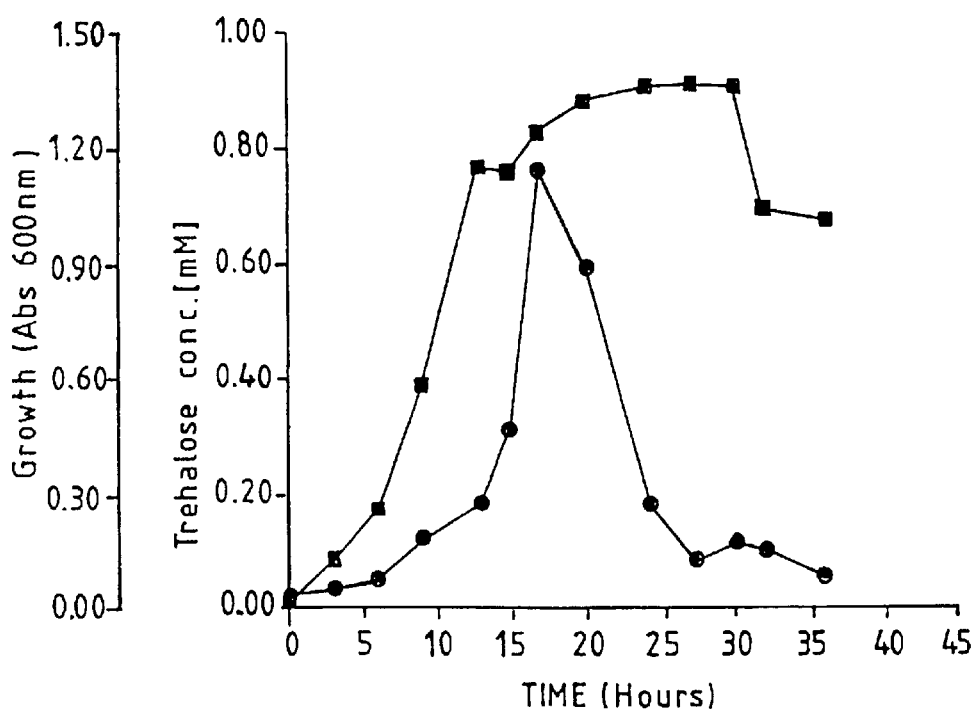
FIGS. 6A and 6B are graphs depicting the effect of a high osmolarity condition (0.5M NaCl) on intracellular trehalose concentration.
Figure 6B:
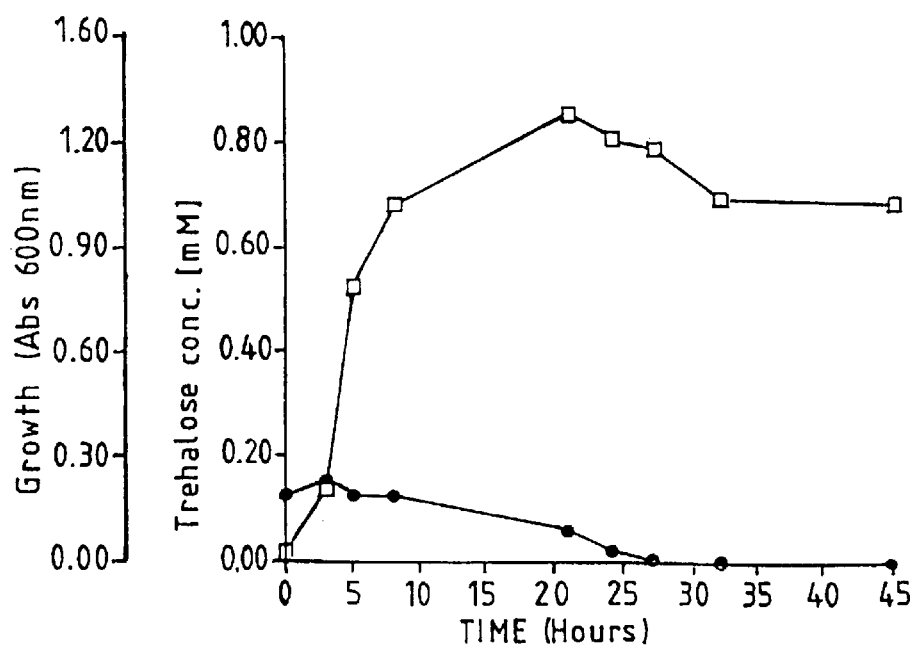

The time required for stimulating intracellular trehalose production depends, inter alia, on the nature of the prokaryotic cells (including genus, species, and/or strain) and the conditions under which trehalose induction occurs (i.e., whether by osmotic shock, oxygen deprivation, etc.). For trehalose induction by osmotic shock, the time required for maximum concentration of intracellular trehalose in turn depends on the degree of osmolarity as well as the particular salts used. For example, in E. coli, ammonium sulfate (($NH_4)_2SO_4$) stimulates about half the amount of intracellular trehalose concentration as NaCl, $CaCl_2$ or KCl. For E. coli in 0.5 M salt minimal media, maximum intracellular trehalose concentration occurs within about 10–17 hours, with significant induction by 17 hours after osmotic shock (Example 1; FIG. 6).

As is readily apparent to those skilled in the art, achieving a desired intracellular trehalose concentration can also be effected by other means such as introducing trehalose into the cell(s). This can be accomplished, for example, by culturing cells in the presence of trehalose while subjecting the cell(s) to conditions that permeabilize the cell wall and membrane. Examples of such conditions include, but are not limited to, conditions that effect membrane phase transition (such as cycles of cooling and warming or osmotic shock) and electroporation. The intracellular trehalose concentration can be determined for these conditions as described above. Conditions that effect membrane phase transition especially apply to Gram negative bacteria.

Accordingly, one embodiment of the present invention is a method of preserving prokaryotic cells comprising the steps of culturing the prokaryotic cells under conditions that increase intracellular trehalose concentration to a level effective to increase storage stability in the methods described herein, mixing the prokaryotic cells with a drying solution which contains a stabilizing agent, and drying the prokaryotic cells such that a glass is produced having less than about 5% residual moisture.

Mixing the prokaryotic cells with drying solution. After intracellular trehalose is increased to the desired degree, the prokaryotic cells are harvested by, for instance, centrifigation and resuspended in a drying solution containing a stabilizing agent, preferably a non-reducing carbohydrate such as trehalose.

Particularly preferred non-reducing carbohydrates are trehalose, maltitol (4-O-β-D-glucopyranosyl-D-glucitol), lactitol (4-O-β-D-galactopyranosyl-D-glucitol), palatinit [a mixture of GPS (α-D-glucopyranosyl-1→6-sorbitol) and GPM (α-D-glucopyranosyl-1→6-mannitol)], and its individual sugar alcohol components GPS and GPM and hydrogenated maltooligosaccharides and maltooligosaccharides.

In addition to trehalose, suitable stabilizing agents include, but are not limited to, non-reducing glycosides of polyhydroxy compounds selected from sugar alcohols and other straight chain polyalcohols. Other useful stabilizing agents include neotrehalose, lactoneotrehalose, galactosyltrehalose, sucrose, lactosucrose, raffinose, stachyose and melezitose. Carbohydrates with mild reducing activity, such as maltohexose, maltoheptulose, Sepharose and Dextran, can also be used with Maillard reaction inhibitors as described in patent application PCT/GB95/01967. Maillard reaction inhibitors can also be used to improve the performance of unstable reducing carbohydrates such as sucrose.

The concentration of non-reducing carbohydrate(s) in the drying solution will depend on several variables, most particularly the genus, species, and/or strain of prokaryotic cell that is being stabilized and the method of drying. For $E. coli$, the non-reducing carbohydrate (trehalose) concentration is preferably at least about 25%, more preferably at least about 35%, even more preferably at least about 45% (w/v). Preferably, the carbohydrate concentration should be less than about 50%, as higher concentrations may interfere with effective drying.

The solvent(s) that forms the basis for the drying solution can be any of a number of substances, provided it does not significantly affect cell viability. Preferably, the solvent is aqueous.

The drying solution can optionally contain additives that contribute to overall stability of the prokaryotic cells. Generally, preferred additives increase the viscosity of the drying solution, which in turn enhances the drying process by more efficient foam production with higher $T_g$s. Examples of additives include, but are not limited to, polyvinylpyrollidone (Kollidon Series: 12, 17, 25, 30, 90; BASF), carboxymethyl cellulose (Blanose HF; Aqualon) hydroxypropyl cellulose and hydroxyethyl starch (HES; MW 200,000). Preferably, Kollidon 90 is present in the drying solution at a concentration of about 1.5%. Preferably, the concentration of carboxymethyl cellulose is about 0.1%. Particularly preferred is a drying solution containing about 45% trehalose and either about 1.5% Kollidon 90 or about 0.1% carboxymethyl cellulose. Other additives that can be used include volatile salts, which contribute to effective drying (via foam formation). Examples of volatile salts include, but are not limited to, ammonium bicarbonate, ammonium chloride, ammonium acetate and ammonium sulfate. However, when using these salts, it is possible that more effective drying may be counteracted by lower viability due to pH and salt-specific effects.

The volume of the drying solution added to the prokaryotic cells, and thus the density of the prokaryotic cells in the drying solution, can vary. However, too low a cell density proportionately increases the drying time per cell; too high a density may adversely affect rapidity and/or efficiency of foam formation and thus drying. Moreover, too high a cell density could result in higher concentration of anti-foaming agents produced by the cells. Preferably, the cell density is about 4 to $8 \times 10^9$ cells (CFU) per ml, although densities as high as $2 \times 10^{10}$ cells per ml have been used with success. Generally, the volume of drying solution is significantly less than the volume of culture medium used for increasing intracellular trehalose concentration. The optional volume will vary somewhat on the types of cells and solutes and can be readily determined empirically.

Drying the prokaryotic cells. Upon suspending in the drying solution, the prokaryotic cells are then dried such that a glass is formed. Drying can be effected using methods known in the art, including, but not limited to, air (i.e., ambient temperature) drying, spray drying, and freeze drying. As used herein, the glass containing the dried prokaryotic cells preferably has a residual moisture content less than about 5%.

Drying is preferably performed at pressure less than ambient (i.e., vacuum). Preferably, the pressure is about 0.1 to 0.075 Torr/mm Hg. More preferably, the pressure is about 0.075 to 0.05 Torr/mm Hg. Most preferably, the pressure is about 0.05 to 0.03 Torr/mm Hg and external temperature is about 40° C.

Preferably, drying occurs above freezing temperatures and under a vacuum such that a foamed glass matrix (FGM) is formed. PCT/GB96/01367. Vacuum drying under freezing conditions will lead to lower viability. For creation of a vacuum, any vacuum drier with a control, preferably programmable control, of the vacuum pressure and external temperature can be used. As an example, a pump is capable of providing a vacuum of 0.01 Torr/mm Hg and evacuating the product chamber down to 0.2–0.01 Torr/mm Hg in 15–20 minutes. The machines used in the present work were the FTS Systems Inc. (Stone Ridge, N.Y.) Model TDS 0007-A with a VP-62P vacuum pump and a FD-0005-A condenser module or the Labconco, Inc. (Kansas City) Model No. 77560 with a Lyph-Lock 12 condenser unit and an Edwards E2M8 two-stage vacuum pump.

Reduction of the external pressure has at least two desirable effects. First, it reduces the vapor pressure of the solvent in the gas phase, thus accelerating evaporation and drying. The increased rate of evaporation causes evaporative cooling unless external heat is applied to replace the latent heat of evaporation. Under vacuum, the rate of drying is limited by this energy input. Thus, the effect of increasing the external temperature is, surprisingly, to accelerate the rate of drying and not to increase the sample temperature. The second effect of reduced external pressure is to drastically lower the boiling point of the sample. Boiling can therefore be conducted by a very modest rise in sample temperature which does not have a deleterious effect on the product.

Preferably, drying occurs in two stages: first, holding external temperature constant for a period of time; and second, increasing the external temperature until drying is complete. The temperature can be increased gradually, for example, 10 degrees over an hour, or, more preferably the temperature can be increased in equal increments, with each increment held constant for a period of time. In one embodiment, the temperature is maintained at about 40° C. for about 16 hours, followed by gradually increasing the temperature to about 80° C. over about the next 4 hours.

In a preferred embodiment, the prokaryotic cells are dried as follows: the pressure is adjusted to 30 mT, with initial shelf temperature of 40° C. for 16 hours; followed by incrementally increasing the shelf temperature to 80° C. at a rate of 2.5° C. per minute in increments of 2° C., while holding each increment for about 12 minutes. Following this protocol, foaming typically occurs within 60 minutes oft he initiation of drying, and the drying procedure is completed within 24 hours without substantially compromising viability. Example 6 provides a protocol.

FGMs are also formed by evaporating bulk solvent from the drying solution to obtain a syrup, exposing the syrup to a pressure and temperature sufficient to cause boiling or foaming of the syrup, and removing moisture so that residual moisture does not exceed about 4%, preferably about 3%, more preferably about 2.5%.

In the primary drying step, the solvent is evaporated to obtain a syrup. Typically, a "syrup" is defined as a solution with a viscosity in the region of $10^6$–$10^7$ Pascal seconds. The syrup is not defined as a fixed concentration, but is a result of the bulk of the solvent evaporating from the mixture. Typically, a syrup is a viscous mixture containing the glass matrix-forming material and/or additives and/or prokaryotic cells, in a significantly higher concentration than that of the initial mixture. Typically, the evaporation step is conducted under conditions sufficient to remove about 20% to 90% of the solvent to obtain a syrup. The viscosity of the syrup is preferably such that when the syrup boils, evaporation from the increased surface area, provided by extensive bubble formation, results in its vitrification.

Under the vacuum, rapid drying continues until the viscosity of the sample begins to increase. At this point, the reduced mobility of water molecules through the viscous syrup reduces the rate of evaporative cooling and the sample temperature rises until it reaches the boiling point at the reduced pressure. On boiling, a large increase in the area of the liquid/gas interface occurs due to the bubbling of the syrup. This increased evaporative surface causes a sharp increase in the drying rate and the liquid foam dries into solid glass foam (FGM). Typically, this occurs soon after boiling.

Temperatures for the boiling step can be above or below ambient temperature. Preferably, the external temperature for the boiling step is about 5 to 80° C. More preferably, the external temperature is about 5 to 60° C.; even more preferably, about 5 to 35° C.

The drying process results in formation of bubbles which greatly increases the evaporative surface area of the syrup. This allows increased evaporation of residual solvent and the FGM vitrifies as a solid foam of the bubbles which result from the boiling step. The endpoint of the boiling step can be determined by an increase in sample temperature, which is preferably maintained for a period of time sufficient to ensure complete drying. The optimum time varies from sample to sample but is easily determinable by one of skill in the art.

Various container shapes and sizes can be processed simultaneously. Ideally, the container size used is sufficient to contain the initial mixture and accommodate the volume of the dried cells formed thereof. Generally, 3 ml pharmaceutical vials are used. Any such vials can be used, including Wheaton molded and tube-cut vials. Preferably, the vials are moisture resistant so as to eliminate any deleterious effects due to moisture uptake by a sample.

Residual moisture content can be measured using assays known in the art, such as Karl Fischer coulometric method and gravimetric method. For determination of residual moisture using a Coulometer, residual moisture is extracted using formamide, followed by measurement using a Coulometer. Percent moisture in the sample (w/w) is determined using the following formula:

$$\frac{\text{test sample} - \text{blank} \times 10^3 \times 10^2}{\text{wt of dried sample (mg)} \times 10^2 \times 10^3} \% \text{ residual moisture}$$

A more detailed description of this assay is provided in Example 2. Preferably, residual moisture will be equal to or less than about 5%, more preferably less than about 4%, more preferably equal to or less than about 3% even more preferably equal to or less than about 2.5%. When cells are dried more rapidly by gradually increasing the temperature, as described above, residual moisture may drop below 2%. The allowable maximum for different cell types can easily be determined empirically. Generally, residual moisture above about 5% can be detrimental to viability. This varies depending, inter alia, on the genus/species/strain used, the concentration and type of non-reducing carbohydrate used in the drying solution, method of drying and type of storage.

Figure 4:
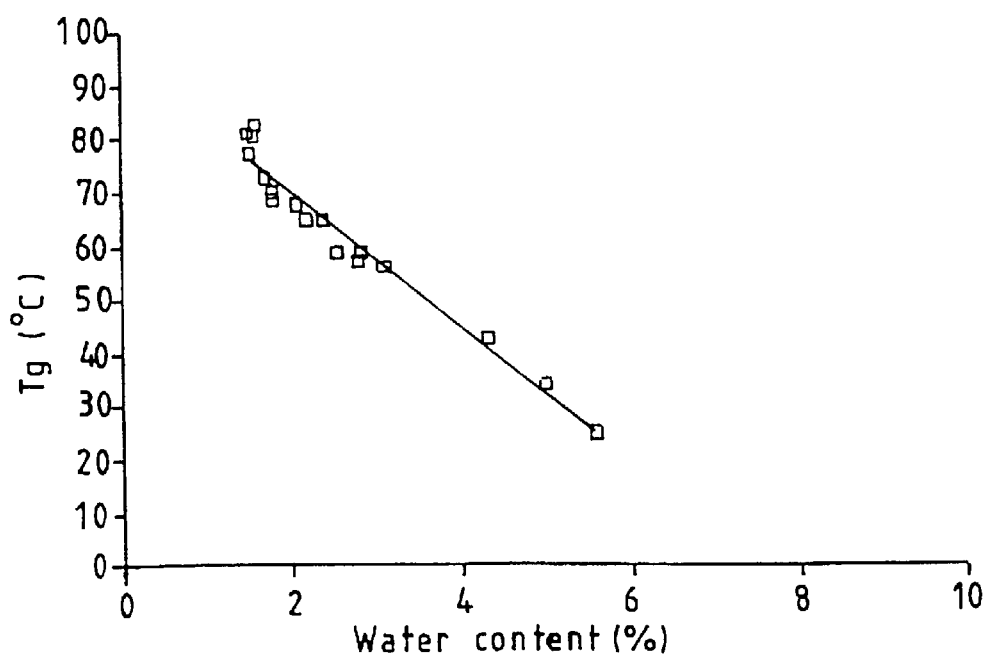
FIG. 4 is a graph depicting the relationship between $T_g$ and residual moisture in a formulation of 45% trehalose and 1.5% Kollidon 90.

The resultant glass or FGM containing the dried, stabilized prokaryotic cells should have a $T_g$ sufficiently high to preserve the cells. "$T_g$" refers to the temperature at which the glass undergoes a transition into liquid phase. Variables that determine $T_g$ include, but are not limited to, the amount of residual moisture of the dried preparation(s) and the type of stabilizing agent used. Generally, protein and polysaccharides raise $T_g$, while salts generally lower $T_g$. FIG. 4 illustrates the relationship between $T_g$ and percent residual moisture.

For purposes of this invention, $T_g$ should be at least about 70° C., preferably at least about 75° C., more preferably at least about 80° C., even more preferably at least about 85° C., most preferably at least about 90° C. $T_g$ can be determined using standard techniques in the art, such as differential scanning calorimetry. Generally, the higher the $T_g$, the higher the allowable storage temperature.

Figure 5:
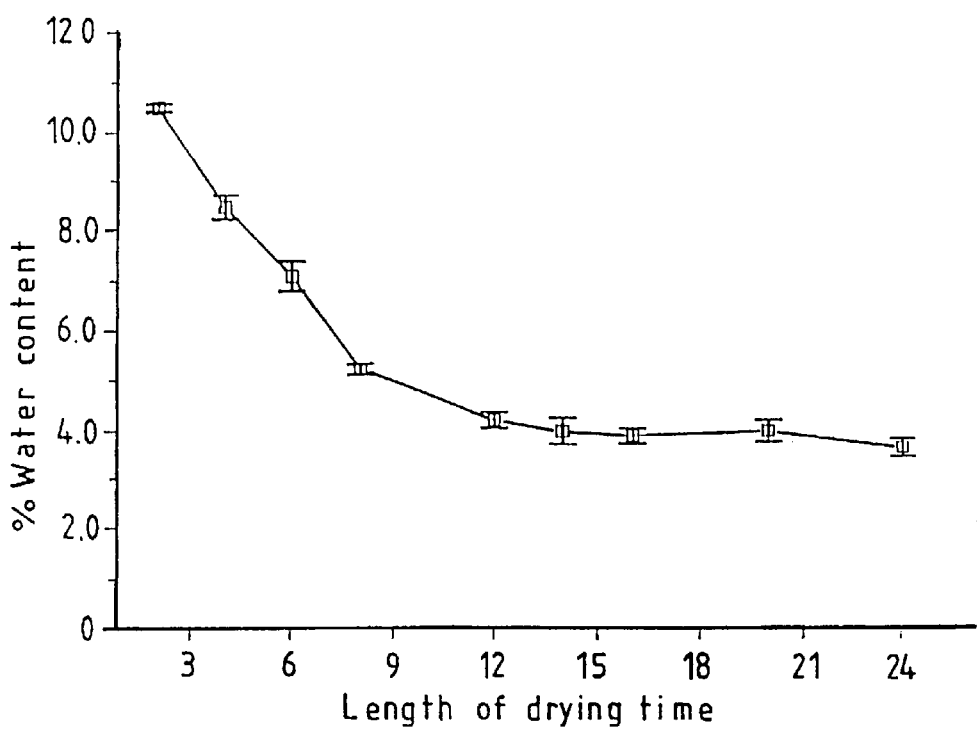
FIG. 5 is a graph depicting the relationship between residual moisture and length of drying time in a formulation of 45% trehalose and 0.1% CMC. The FTS drying protocol was 30 mT ST 40° C. (×hrs).

The length of time required to achieve the desired residual moisture and/or $T_g$ will depend on several variables, including, but not limited to, sample size, pressure and temperature. Generally, the longer the samples are dried, the lower the residual moisture (and hence the greater the $T_g$). FIG. 5 shows the relationship between residual moisture and length of drying time. Drying can be achieved in as few as 20 hours, more generally within about 24 hours. Gradually increasing the temperature during drying, as described above, lowers the drying time without significantly reducing cell viability (Example 6).

Prokaryotic cells dried by the methods disclosed herein can be stored for varying lengths of time at ambient or higher temperatures. The length of time the dried, stabilized prokaryotic cells can be stored will depend, inter alia, on the genus, species, and/or strain of the prokaryotic cell, the degree of intracellular trehalose production and/or concentration, the concentration and type of stabilizing agent in the drying solution, the drying protocol followed, the amount of residual moisture after drying, and the acceptable degree of viability.

Reconstitution of stabilized cells. The prokaryotic cells can be reconstituted after drying by adding a suitable solvent. Thus, the invention includes methods of reconstituting prokaryotic cells that have been obtained by the methods described herein. The nature and amount of solvent used for reconstitution will depend upon the prokaryotic cells as well as their intended use. Such determinations can be made empirically by those skilled in the art. Generally, cells can be reconstituted with an aqueous solvent. If the cells are to be used as a pharmaceutical, reconstitution is preferably with a sterile physiologically acceptable buffer.

If the prokaryotic cells are to be used as a vaccine, and thus as an immunogenic agent, an adjuvant can be added in an amount sufficient to enhance the immune response to the immunogen. The adjuvant can be added to the prokaryotic cells before drying, for example, cholera B toxin subunit can be dried simultaneously with V. cholera. Alternatively the adjuvant can be separately reconstituted along with the prokaryotic cells.

Suitable adjuvants include, but are not limited to, aluminum hydroxide, alum, QS-21 (U.S. Pat. No. 5,057,540), DHEA (U.S. Pat. Nos. 5,407,684 and 5,077,284) and its derivatives (including salts) and precursors (e.g., DHEA-S), beta-2 microglobulin (WO 91/16924), muramyl dipeptides, muramyl tripeptides (U.S. Pat. No. 5,171,568), monophosphoryl lipid A (U.S. Pat. No. 4,436,728; WO 92/16231) and its derivatives (e.g., Detox™), and BCG (U.S. Pat. No. 4,726,947). Other suitable adjuvants include, but are not limited to, aluminum salts, squalene mixtures (SAF-1), muramyl peptide, saponin derivatives, mycobacterium wall preparations, mycolic acid derivatives, nonionic block copolymer surfactants, Quil A, cholera toxin B subunit, polyphosphazene and derivatives, and immunostimulating complexes (ISCOMs) such as those described by Takahashi et al. (1990) Nature 344:873–875.

For veterinary use and for production of antibodies in animals, mitogenic components of Freund's adjuvant can be used. The choice of an adjuvant depends in part on the stability of the vaccine in the presence of the adjuvant, the route of administration, and the regulatory acceptability of the adjuvant, particularly when intended for human use. For instance, alum is approved by the United States Food and Drug Administration (FDA) for use as an adjuvant in humans.

Cell viability (i.e., survival) can be determined using any of a number of techniques known in the art, such as, for example, a plate assay for colony forming units (CFU). Viability can be determined at any time, including before and immediately after the cells are dried as well as upon various times during storage. It may be desirable to test viability after reconstitution but before application and/or administration of the cells.

For a plate assay, cells are reconstituted at desired time(s) with a desired solvent, generally sterile distilled water of a volume at least equal to the volume of the dried cells. After vortexing, solutions of reconstituted cultures are diluted (generally 10-fold) in minimal media (for example M9 minus a carbon source) and plated in triplicate on appropriate nutrient again within 30 minutes, more preferably within 15 minutes. After incubation at 37° C. for 18–24 hours, the number of colony forming units (CFU) is determined. Survival is calculated as a percentage of zero time colony counts. A more detailed description of the plate viability assay is provided in Example 2.

Compositions of cells made by the methods herein. The invention also encompasses compositions comprising prokaryotic cells obtained by the methods described herein. The compositions include, but are not limited to, dried prokaryotic cells and reconstituted prokaryotic cells made according to the methods described herein. The compositions may further comprise any pharmaceutically acceptable vehicle or excipient, which are well known in the art.

The following examples are provided to illustrate but not limit the invention. S. typhimurium 1344 and S. typhi Ty21a were obtained from the National Institute of Biological Standards and Control, South Mimms, UK.

EXAMPLE 1

Effect of Osmotic Shock on Production of Intracellular Trehalose in E. coli

E. coli NCIMB strain 9484 was cultured in Evans medium (pH 7.0; Table 1) containing one of a variety of agents for increasing osmotic pressure. After overnight incubation at 37° C. in initial Evans medium, a 4 ml culture of E. coli grown in Evans medium under nitrogen limitation was used to inoculate a 200 ml culture of Evans medium osmotic shock.

TABLE 1

| Evans medium and Evans osmotic shock medium | | |
|---|---|---|
| | Initial Evans Medium | Osmotic Shock Evans medium |
| glucose | 140 mM | 10 g/l glucose |
| $NH_4Cl$ | 5 mM | 3–5 g/l $NH_4Cl$ (15 mM) |
| KCl | 5 mM | 0.5 M NaCl = 29.22 g/l |
| $Na_2SO_4$ | 1.8 mM | 1.8 mM |
| citric acid | 1 mM | 1 mM |
| $MgCl_2$ | 0.3 mM | 0.3 mM |
| $CaCl_2$ | 0.5 mM | 0.5 mM |
| $NaH_2PO_4$ | 5.6 mM | 5.6 mM |
| $Na_2HPO_4$ | 20 mM | 20 mM |
| $ZnSO_4$ | 3.8 mM | 3.8 mM |
| $FeCl_2$ | 50 mM | 50 mM |
| $MnCl_2$ | 25 mM | 25 mM |
| $CuCl_2$ | 2.5 mM | 2.5 mM |
| $H_3BO_3$ | 2.5 mM | 2.5 mM |
| $CoCl_2$ | 0.5 mM | 0.5 mM |
| chloramphenicol | 50 mg/liter | 50 mg/liter |

Intracellular trehalose concentration was measured as described below at various times after the initiation of osmotic shock.

Determination of Intracellular Trehalose Concentration

Intracellular concentration of trehalose was determined using high pressure liquid chromatography (HPLC) as follows. Trehalose standards were prepared by first making 10 mM trehalose in 70% ethanol, followed by 10-fold serial dilution from 10 mM to 10 nM using 70% ethanol as diluent. Thirty µl of the standard was 10 placed in a microtube which was placed in an 80° C. water bath for 5 minutes, while noting the initial volume of the supernatant following incubation. Microtubes were centrifuged at 13,000 rpm for 10 minutes and the supernatant removed. After adding an equal volume of chloroform to the supernatant, the samples were vortexed and centrifuged at 13,000 rpm for 10 minutes. The chloroform extractions were repeated another two times. The final volume of the supernatant was adjusted to 500 µl using deionized water. A calibration curve was generated by testing samples at varying concentrations.

Cell samples were prepared for analysis by disrupting the cell wall by sonication (any other method such as mortar and pestle, osmotic lysis, beads can be used) coupled with the preferential solubilization of trehalose in 70% ethanol, followed by removing triglycerides by chloroform extraction. One ml of cell suspension was aliquoted into a microtube, which was centrifuged at 13,000 rpm for 10 minutes. The pellet was resuspended with 100 µl of 70% ethanol (initial volume). The pellet volume was determined by measuring the relative increase in the initial volume following resuspension of the cells. The cell suspension was incubated in a water bath at 80° C. for 5 minutes. The tubes were centrifuged at 13,000 rpm for 10 minutes and the supernatant removed. An equal volume of chloroform was added and the centrifugation step repeated. Chloroform extraction was performed a total of three times. The final volume of supernatant was adjusted to 500 µl using deionized water.

Quantitation of trehalose was achieved by HPLC (Beckman Instruments), using a Dionex CarboPac PA 100 analytical column, with a Dionex ED40 pulsed amperometric electrochemical detector. Total trehalose concentration from the original cell pellet was determined as a fraction of the final volume extracted and the pellet volume multiplied by the trehalose concentration determined using the following formula:

$$\frac{\text{Final volume of supernatant}}{\text{Pellet volume}} \times \text{Trehalose concentration}$$

Final volume of supernatant was the aqueous volume remaining after the final chloroform extraction. Pellet volume was the difference in the resuspended pellet following the addition of 100 µl of 70% ethanol. Concentration of trehalose formed was determined using the trehalose concentration curve.

The results obtained are shown in FIG. 6. Significant increases in intracellular trehalose concentrations were observed at 15–17 hours after initiation of osmotic shock, with values peaking at less than 20 hours.

EXAMPLE 2

Stabilization and Reconstitution of *E. coli* using Trehalose

*E. coli* (strain 9484) was placed in 100 ml batch cultures of a minimal medium related to M9 (minimal medium) but with high (0.5 M) salt content ($Na_2HPO_4$, 6 g/l; $KH_2PO_4$, 3 g/l; $NH_4Cl$, 0.267 g/l; NaCl, 29.22 g/l; 1 M $MgSO_4$, 1 ml/l; 0.1 M $CaCl_2$, 1 ml/; thiamine HCl, 1 ml/l; glucose at final concentration of 2.5% w/v). This is "modified M9 medium." Cells were grown for 22 hours at 37° C. with shaking. A control culture where the medium was supplemented with 20 mM betaine, in which trehalose synthesis would be markedly reduced, was also prepared. Samples of cultures were removed for trehalose determination (3×1 ml) as described in Example 1 and protein estimation by the Bradford assay (3×10 ml; Bio-Rad).

Two 25 ml aliquots of the test and control culture were harvested by centrifugation at 10,000 rpm for 10 minutes. Cell pellets were resuspended in 5 ml of 45% trehalose, 1.5% polyvinylpyrollidone (Kollidon 90; BASF) or 0.1% carboxymethylcellulose (Blanoes HF; Aqualon). The suspensions were then pooled to a total volume of 10 ml with a typical density of 4–8×10^9 bacteria/ml and 300 µl aliquots dispensed into 3 ml pharmaceutical vials.

Bacteria were dried under vacuum without freezing in a modified FTS freeze dryer according to the following protocol: vacuum, 30 mT; initial shelf temperature 40° C. for 16 hours, followed by ramping to 80° C. at a rate of 2.5° C. per minute in increments of 2° C. with a holding time of 12 minutes per increment. Foaming occurred within approximately 60 minutes of initial drying.

Residual moisture content was determined as follows. One ml of formamide was carefully dispensed into each vial containing the dried bacteria in trehalose. One ml of formamide added to an empty vial served as a control. Residual moisture was extracted by mixing for 15 to 20 minutes at room temperature. For the analysis, 100 µl of the blank (control) formamide was added to a reaction vessel using disposable needles and syringes, and the value registered by the Coulometer (Karl/Fischer) was recorded. Care was taken not to introduce air into the formamide samples, as air contains water vapor. The test (and control) samples were measured in duplicate. The value determined by the Coulometer was equal to µg of water. Test sample less blank divided by 100 is equal to µg of water per µl of formamide in the sample. Percent moisture in the dried sample (w/w) is:

$$\frac{\text{test sample} - \text{blank} \times 10^3 \times 10^2}{\text{wt of dried sample (mg)} \times 10^2 \times 10^3}\%$$

Viability was determined immediately after completion and at various times during storage at 37° C. using a plate assay. For the plate assay, serial 10-fold dilutions of cells were set up by using minimal medium minus a carbon source as a sterile diluent.

Thirty µl of the cell suspension from the sixth dilution tube was added to each of 3 LB (Luria-Bertuni) plates, using a sterile glass spreader to spread the culture over the entire surface of the plate. The plates were incubated overnight at 37° C., and the colonies counted.

X=number of colonies X×33–⅓×1×10^6 dilution section CFU/ml

The results for storage at 37° C. up to 45 days are shown in FIG. 3. Greater than 50% viability (typically 50–80%) in the trehalose induced cells was observed in samples reconstituted immediately after drying. More significantly, no further losses in viable cell recovery were observed on storage of the dried cells, even after 45 days storage at 37° C. (FIG. 3.).

EXAMPLE 3

Southern Blot Analysis to Detect Presence of Trehalose Synthase Gene

DNA was prepared from *E. coli, S. typhimurium* 1344 (1344), and *Salmonella typhi* Ty21a (Ty21a) using standard methods. *E. coli* and *Salmonella* genomic DNA were digested with restriction endonucleases Hind III (H), EcoRI (R), or Bam H1 (B), separated on a 0.8% TBE (Tris-borate electrophoresis buffer) agarose gel and blotted onto nylon filters. The filters were screened using a $^{32}P$-labeled probe corresponding to the otsA/B region of *E. coli* that codes for the trehalose synthase genes in *E. coli*. After hybridization, the filters were washed at low stringency. Exposure of the gels to X-Ray film was overnight for *E. coli* and three days for *Salmonella spp.*

The presence of trehalose synthase genes was detected in both strains of Salmonella as shown in FIG. 2. Fainter bands were detected when filters were washed under higher stringency conditions.

EXAMPLE 4

Induction of Trehalose Synthesis in Salmonella

Figure 7:
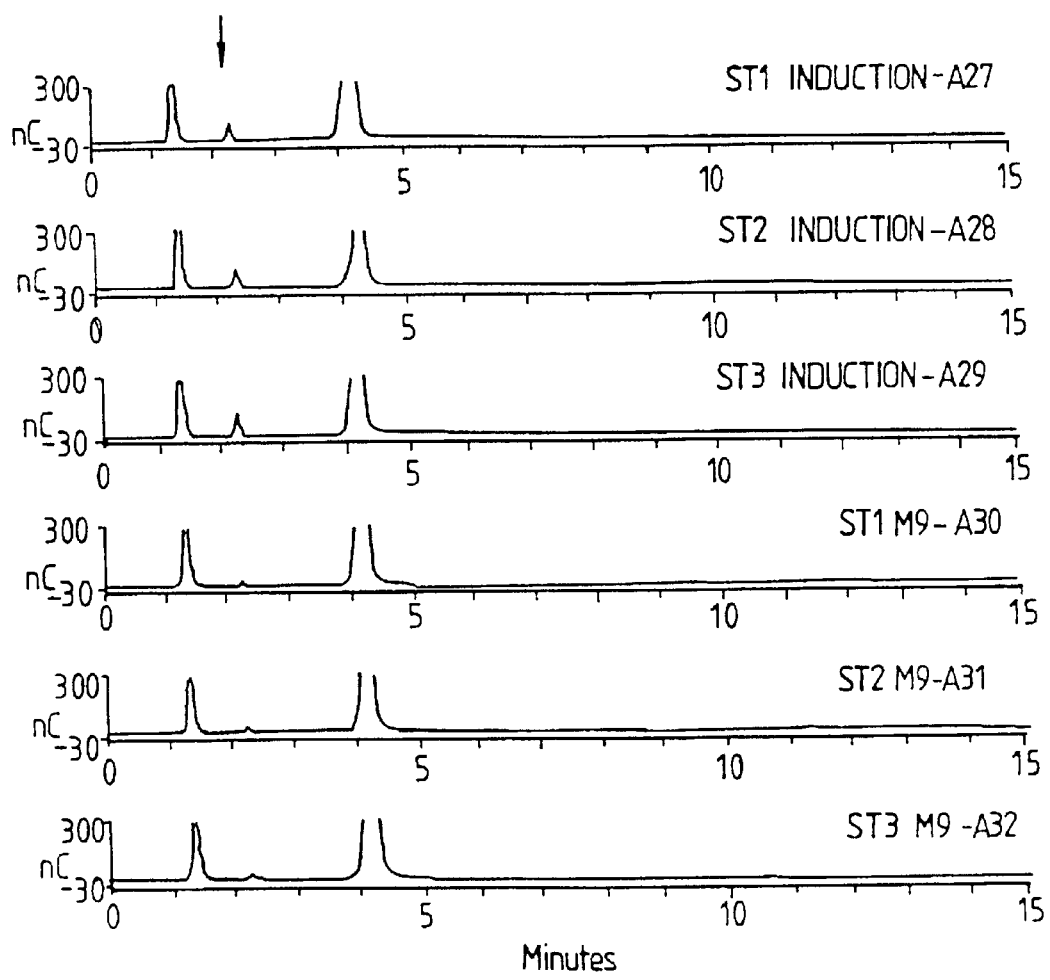
FIG. 7 is a reproduction of a series of tracings from a HPLC analysis of intracellular trehalose concentration in Salmonella before and after trehalose induction by osmotic shock.

*Salmonella typhimurium* (1344) was grown overnight at 37° C. in either M9 (minimal) medium with and without 0.5 M NaCl. Cells were harvested by centrifugation and analyzed for intracellular trehalose concentration by HPLC analysis as described in Example 1. The results are shown in FIG. 7. Growth in high salt medium showed a 4 to 5 fold induction of trehalose synthesis.

EXAMPLE 5

Relation Between Tg and Residual Moisture

*E. coli* (strain 9484)were grown in M9 media containing high salt as described in Example 2. For drying, cells were suspended in an aqueous drying solution containing 45% trehalose and 1.5% Kollidon 90 and dried for 3–24 hrs under vacuum as described in Example 2. Cells were collected at various times, and the residual water content and Tg were measured on aliquots of the same sample to eliminate any possible vial-to-vial variation. The results of the relationship of Tg and residual moisture are shown in FIG. 4.

EXAMPLE 6

Comparison of Effect of Slower and Faster Drying on Viability

E. coli (strain 9484)were grown in modified M9 media described in Example 2. For drying, cells were suspended in an aqueous drying solution containing 45% trehalose and 0.1% carboxymethyl cellulose (Blanose H. F., Aqualon).

Two different drying protocols were followed: (a) pressure, 30 mT; external temperature 40° C. for 16 hours, followed by increasing (ramping) the temperature to 80° C. at the rate of 0.04° C./minute in increments of 2° C., holding each increment for about 60 minutes (slow drying); (b) pressure, 30 mT; external temperature 40° C. for 16 hours, followed by increasing the temperature to 80° C. at the rate of 2.5° C./minute in increments of 2° C., holding each increment for about 12 minutes (fast drying).

Viability was measured immediately after drying. The samples prepared by fast drying were no less viable than those samples prepared by slow drying. Ranges between about 48% and 52% were observed for the "fast" dried samples, while between about 40% and 52% were observed for the "slow" dried samples. On average, the "fast" dried samples displayed higher viability than the "slow" dried samples.

Figure 8:
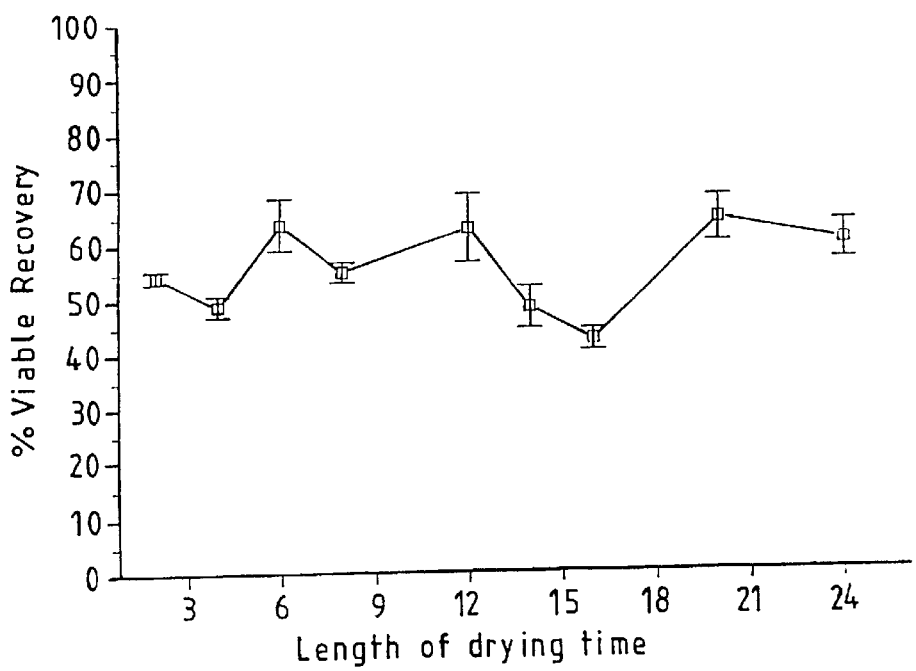
FIG. 8 is a graph depicting the relationship between cell viability and length of drying time in a formulation of 45% trehalose and 0.1% CMC. The FTS drying protocol was 30 mT ST 40° C. (×hrs).

The effect of length of drying time on viability is shown in FIG. 8. The drying solution contained 45% trehalose and 0.1% CMC; the FTS drying protocol was 30 mT at 40° C. for varying times.

EXAMPLE 7

Comparison of the Effects of Different Excipients on Stabilising the Outer Membrane of E. coli 9894 Following Intracellular Induction of Trehalose E. coli strain 9894 was inoculated in 100 ml batch cultures of minimal medium related to M9 but with high (0.5M) salt content as described in Example 2. Cells were grown for 22 hours at 37° C. in a shaking incubator (early stationary phase). Samples of cultures were removed for trehalose determination (3×1 ml) and protein estimation by the Bradford assay (3×10 ml; Bio-Rad). Trehalose concentration was expressed as $\mu$mol (mg protein)$^{-1}$.

Intracellular concentration of trehalose was determined using ion exchange chromatography with electrochemical detection. Calibration standards were prepared by first making a stock solution of 1 mM trehalose, glucose, sucrose and maltose standards in water, followed by serial dilutions from 1 mM to 2.5 $\mu$M using water as a diluent.

One ml of cell suspension was aliquoted into a microtube, which was centrifuged at 13,000 rpm for 10 minutes and the supernatant removed. The cell pellet was resuspended in 200 $\mu$l of 80% ethanol. The cell suspension was prepared for analysis by disrupting the cell wall in a 80° C. bath for 10 minutes, coupled with preferential solubilisation of all intracellular sugars in 80% ethanol. The suspension was centrifuged and the supernatant removed. An equal volume of chloroform was added to the supernatant and vortexed, and the sample was centrifuged removing triglycerides by the chloroform extraction. The aqueous layer was transferred into a fresh Eppendorf tube and the chloroform extraction repeated. The aqueous layer was aliquotted into HPLC vials and vacuum dried, followed by rehydration using 500 $\mu$l sterile water.

Quantitation of trehalose was achieved by HPLC (Dionex DX-500), using a Dionex CarboPac PA analytical column, with a Dionex ED40 pulsed amperometric electrochemical detector. The concentration of trehalose was determined from the calibration curve.

Two 30 ml aliquots from each flask were harvested by centrifugation at 10,000 rpm for 10 minutes. Cell pellets were resuspended in 8 ml of 25–45% sugar, 0.1% CMC (sodium carboxymethyl cellulose; Blanose 7HF; Aqualon). The suspensions were then pooled to a total volume of 16 ml with a typical cell density of 4–8×10$^9$ CFU/ml and 300 $\mu$l aliquots dispensed into 3 ml pharmaceutical vials.

Bacteria were dried under vacuum without freezing using the following protocol: vacuum, 30 mT; initial shelf temperature 40° C. for 16 hours, followed by ramping to 80° C. at a rate of 2.5° C./min in increments of 2° C. with a holding time of 12 minutes per increment. Foaming occurred between 60–120 minutes of initial drying.

Viability was determined immediately before and after the completion of the drying procedure and at various times during storage at 37° C. using a plate assay as described in Example 2. The residual moisture content and the glass transition temperature were also determined.

The results for storage at 37° C. are shown in Table 2. No significant loss in viable cell recovery was observed after 6 weeks storage of E. coli at 37° C. using the non-reducing sugars trehalose, palatinit or lactitol as excipients for stabilizing the outer membrane. More significantly, greater than 99% loss was observed for the reducing sugar glucose.

TABLE 2

E. coli 9484 viable cell recovery immediately after completion of Q-T4 drying and following 3 and 6 weeks storage at 37° C.

| | % Viable Cell Recovery after storage at 37° C. | | |
|---|---|---|---|
| Excipient | Day 0 | Week 3 | Week 6 |
| Trehalose | 36 | 52 | 45 |
| Palatinit | 49 | 49 | 51 |
| Lactitol | 42 | 36 | 34 |
| Glucose | 0.8 | 0.1 | 0.05 |

EXAMPLE 8

Comparison of Q-T4 (the Method of Example 2) and Freeze-dried E. coli

E. coli NCIMB strain 9484 was inoculated in 250 ml batch culture of modified M9 medium. The composition of this medium was described in Example 2. Cells were grown for 24 hours at 37° C. in a shaking incubator until early stationary phase. Samples of cultures were removed for trehalose determination (6×1 ml) and protein estimation by the Bradford assay (5×10 ml) as described in Example 7.

Eight 25 ml aliquots were removed from the flask and the bacteria harvested by centrifugation at 10,000 rpm for 10 minutes. Cell pellets were resuspended in 8 ml of 45% trehalose, 0.1% CMC (sodium carboxymethyl cellulose; Blanose 7HF; Aqualon). The cell suspensions were then pooled to a total volume of 64 ml with a typical cell density of $0.5-1.2\times10^9$ CFU/ml. 300 μl and 500 μl aliquots were dispensed into 3 ml pharmaceutical vials for foaming and freeze-drying procedures respectively.

The bacteria were dried under vacuum without freezing using the Q-T4 foaming protocol as described Example 2. The bacteria were freeze-dried using the following protocol: ramp at 2.5° C./min to an initial shelf temperature of −40° C.; primary drying was performed at a vacuum pressure of 30 mT at −40° C., held for 40 hours; secondary drying was performed by a ramp at 0.05° C./min from −40 to 30° C. and holding for 12 hours.

Viability was determined immediately before and after the completion of the drying procedures and after 3 weeks storage at 37° C. using a plate assay as described in Example 2. The residual moisture content and the glass transition temperature were also determined.

The results for storage at 37° C. are shown in Table 3. No significant loss in bacterial viability was observed after 3 weeks storage at 37° C. in either the bacteria dried by the Q-T4 method or the freeze-dried bacteria. The residual moisture content and the glass transition temperature for the Q-T4-dried bacteria was 1.85±0.2% and 69.05±5.0° C. respectively. The Tg for the freeze-dried bacteria was 104.5±2.1° C. and the residual moisture content was 0.70±0.2%.

TABLE 3

Comparison between Q-T4 drying and freeze drying on viable cell recovery of *E. coli* 9484 after storage at 37° C.

| | % Viable cell recovery after storage at 37° C. | |
| --- | --- | --- |
| | Day 0 | Week 3 |
| Q-T4sys (Drying) | 43.7 ± 10.3 | 45.1 ± 8.5 |
| Q-T4sys (Control) | 2.51 ± 0.2 | <0.01 |
| Freeze Drying | 30.6 ± 3.6 | 30.1 ± 3.7 |
| Freeze Drying (Control) | 1.83 ± 0.6 | <0.01 |

EXAMPLE 9

Intracellular Accumulation of Trehalose During Growth of *S. typhimurium* at 37° C. in a High Salt Medium

*S. typhimurium* 1344 was grown in batch culture in either minimal Salmonella growth medium with or without 0.5M NaCl (NaCl, 29.22 g $l^{-1}$; $(NH_4)_2SO_4$, 0.66 g $l^{-1}$; $K_2HPO_4$, 10.5 g $l^{-1}$; $KH_2PO_4$, 4.5 g $l^{-1}$; $MgSO_4$, 0.1 g $l^{-1}$; tryptophan, 20 mg $l^{-1}$; glucose at a final concentration of 2.5% w/v) for a period of 106 hours at 37° C. Samples were removed periodically for protein measurement by the Bradford Assay and intracellular trehalose determination by HPLC as described in Example 7. Trehalose concentrations were expressed in μmol of trehalose (mg protein)$^{-1}$.

Figure 9:
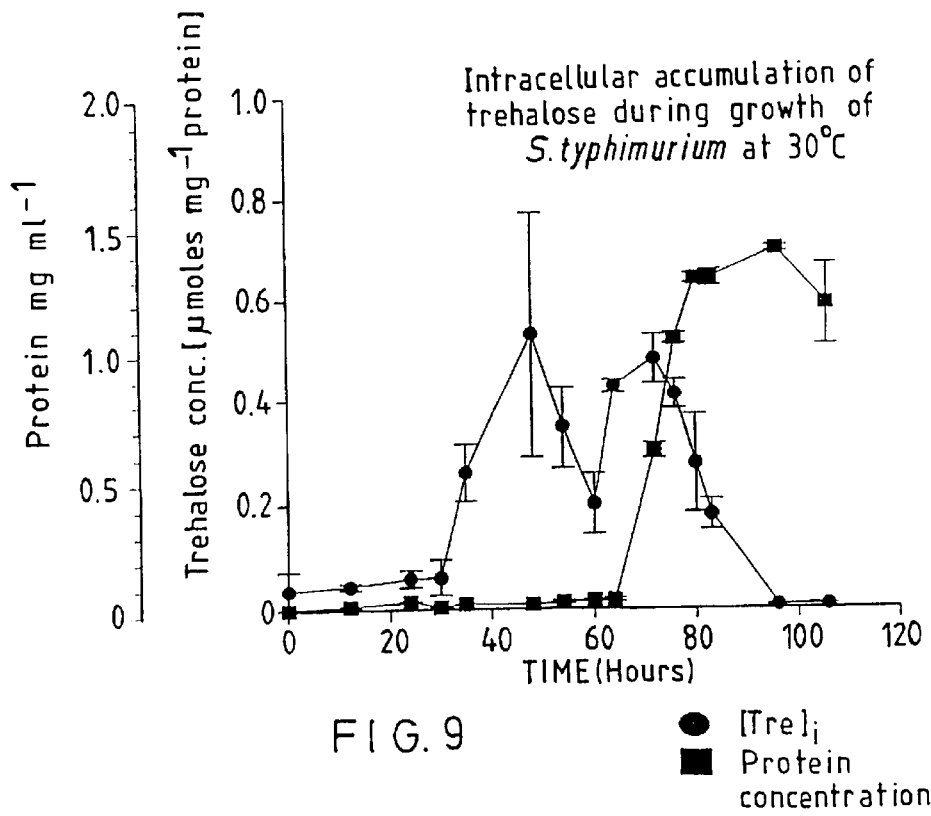
FIG. 9 is a graph depicting intracellular trehalose (●) and protein (■) concentration during growth of *S. typhimurium* at 37° C.

Significant concentrations of trehalose were observed between 30 and 76 hours after inoculation reaching a maximum of 0.53 μmol of trehalose (mg protein)$^{-1}$ after 48 hours as shown in FIG. 9.

EXAMPLE 10

Stabilization of *S. typhimurium* 1344 at 37° C. Using Trehalose

*S. typhimurium* 1344 was grown in batch culture in minimal Salmonella growth medium with 0.5M NaCl. Cells were grown for 60 hours at 37° C. in a shaking incubator and harvested by centrifugation at early stationary phase. A control culture where the basal medium contained no salt was also prepared and harvested at stationary phase in which trehalose synthesis would be markedly reduced, since there is no osmotic stress.

Two 25 ml aliquots from each flask were harvested by centrifugation at 10,000 rpm for 10 minutes. Cell pellets were resuspended and washed in the appropriate growth medium. The resulting cell pellet was resuspended in 8 ml of 45% trehalose, 0.1% CMC (Blanose 7HF; Aqualon). The suspensions were then pooled to a total volume of 16 ml with a typical cell density of $2-4\times10^9$ CFU/ml and 300 μl aliquots dispensed into 3 ml pharmaceutical vials. Bacteria were dried under vacuum without freezing as described in Example 2. Foaming occurred between 60–120 minutes of initial drying.

Samples of cultures (3×1 ml) were removed for trehalose determination and protein estimation by the Bradford assay (3×10 ml; Bio-Rad). Trehalose concentration was expressed as μmol (mg protein)$^{-1}$ as described in Example 7. Viability was determined immediately before and after the completion of the drying procedure and at various times during storage at 37° C. using a plate assay as described in Example 2. The residual moisture content and the glass transition temperature were also determined.

Figure 10:
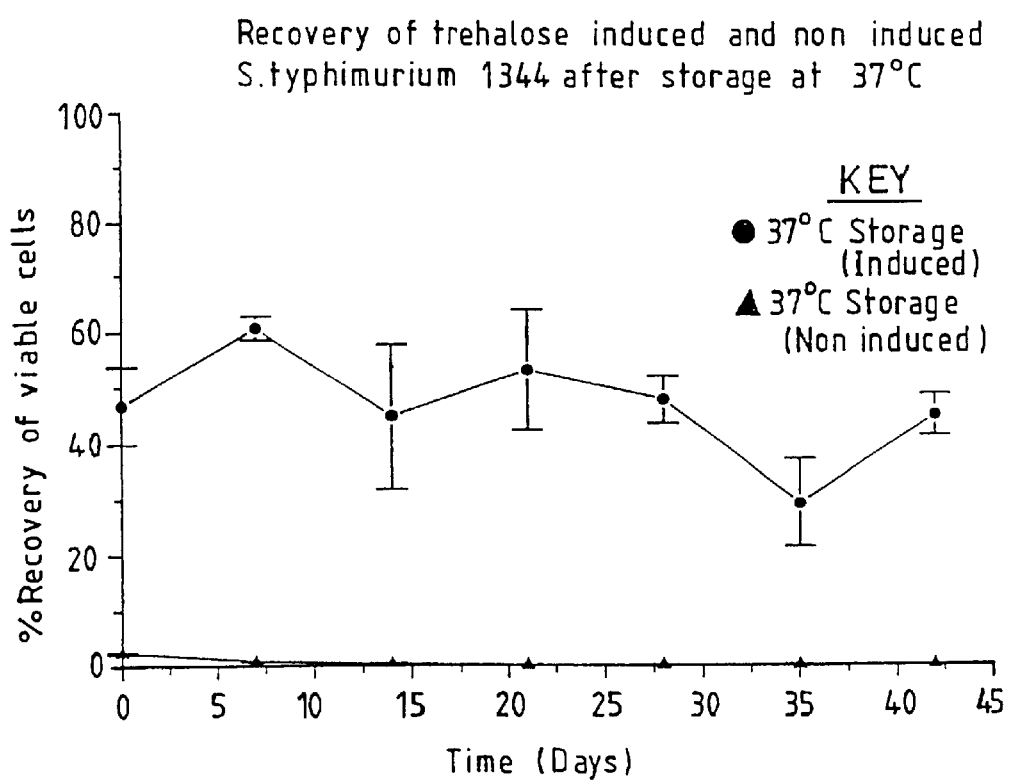
FIG. 10 is a graph depicting the percent recovery of trehalose induced (●) and non-induced (▲) *S. typhimurium* 1344 after storage at 37° C.

The storage results at 37° C. are shown in FIG. 10. No significant loss in viability was observed after 6 weeks storage in *S. typhimurium* 1344, which was osmotically induced to accumulate intracellular trehalose. Significantly, greater than 99% loss was observed for the non-induced bacteria.

EXAMPLE 11

Confirmation of the Presence of the Trehalose-6-phosphate Synthase (otsA) Gene in *E. coli* (NCIMB 9484) and Salmonella spp Extracted genomic DNA from *E. coli* 9484, *S. typhimurium* 1344 and *S. typhi* Ty21a were qualified by OD260/280 nm and agarose gel analysis. Each DNA preparation was prepared separately to ensure no cross-contamination. The DNA was then used to prepare PCR reactions with degenerate primers (where every third base has been substituted either with a selection of bases or an inosine to allow for any sequence changes), Guessmer primers (sequence selection based upon Salmonella specific codon usage) and *E. coli* primers (based purely on *E. coli* sequence) as shown in Table 4. Each set produced at least one positive reaction. The relevant fragments were run on low melting point gels and purified.

TABLE 4 otsA gene probes for *E. coli*, *S. typhimurium* 1344, and *S. typhi* Ty21a

| Target DNA | otsA gene (fragment size/application) | Primer set used |
| --- | --- | --- |
| *E. coli* 9484 | 700 bp/Sequence | *E. coli* based |
| *E. coli* 9484 | 150 bp/Southern Probe | *E. coli* based |
| *S. typhimurium* 1344 | 700 bp/Sequence | Guessmer (Salmonella codon usage) |
| *S. typhimurium* 1344 | 150 bp/Southern probe | Guessmer (Salmonella codon usage) |

TABLE 4-continued otsA gene probes for *E. coli*, *S. typhimurium* 1344, and *S. typhi* Ty21a

| Target DNA | otsA gene (fragment size/application) | Primer set used |
|---|---|---|
| *S. typhi* Ty21a | 700 bp/Sequence | Guessmer (Salmonella codon usage) |
| *S. typhi Ty21a* | 400 bp/Sequence | *E. coli* based |

The 700 bp fragments were ligated into pCR3.1 and then transferred into component cells and sequenced. The resulting sequence data for otsA showed a sequence homology of 77% between *S. typhimurium* 1344 and *E. coli* 9484. The sequence data also demonstrated that only 6 bases from a total of 715 were different between the two Salmonella spp strains.

Although the foregoing invention has been described in some detail by way of illustration and example for purposes of clarity and understanding, it will be apparent to those skilled in the art that certain changes and modifications may be practiced. Therefore, the description and examples should not be construed as limiting the scope of the invention, which is delineated by the appended claims.

We claim:

1. A method of preserving prokaryotic cells comprising the steps of:
   a) increasing intracellular trehalose concentration in the prokaryotic cells to at least 30 mM;
   b) mixing the prokaryotic cells obtained in step a) with a drying solution comprising a stabilizing agent, wherein the stabilizing agent is a carbohydrate; and
   c) drying the product of step b) under conditions sufficient to produce a glass form of the stabilizing agent having less than about 5% (w/w) residual moisture;
   wherein the drying comprises evaporating the solution to obtain a syrup; exposing the syrup to a reduced external pressure and temperature sufficient to cause boiling of the syrup; and removing moisture so that residual moisture does not exceed about 5%;
   wherein the prokaryotic cells retain about 50% to 80% viability upon drying; and
   wherein the prokaryotic cells are *Escherichia coli*.

2. The method according to claim 1, wherein the method of increasing intracellular trehalose concentration is selected from the group consisting of culturing in an osmolarity sufficient to increase intracellular trehalose production, expressing a recombinant trehalose synthase gene or genes and introducing exogenous trehalose.

3. The method according to claim 2, wherein the osmolarity is at least about 350 mOsmoles–1.5 Osmoles.

4. The method according to claim 2, wherein the osmolarity is at least about 400 mOsmoles –1 Osmole.

5. The method according to claim 2, wherein the osmolarity is at least about 300 mOsmoles.

6. The method according to claim 2, wherein the osmolarity is at least about 500 mOsmoles.

7. The method according to claim 2, wherein the osmolarity is increased by adding at least one salt wherein the salt is selected from the group consisting of $Na_2PO_4$, $KH_2PO_4$, $NH_4Cl$, NaCl, $MgSO_4$, $CaCl_2$, thiamine HCl, or any combination thereof.

8. The method according to claim 1, wherein the stabilizing agent is trehalose.

9. The method according to claim 8, wherein the intracellular concentration of trehalose is at least about 100 mM.

10. The method according to claim 1, wherein the stabilizing agent is a non-reducing carbohydrate.

11. The method according to claim 10, wherein the drying solution comprises at least about 25% (w/v) non-reducing carbohydrate.

12. The method according to claim 10, wherein the drying solution comprises at least about 45% (w/v) non-reducing carbohydrate.

13. The method according to claim 10, wherein the non-reducing carbohydrate is selected from the group consisting of trehalose, maltitol (4-O-β-D-glucopyranosyl-D-glucitol), lactitol (4-O-β-D-galactopyranosyl-D-glucitol), palatinit, GPS (α-D-glucopyranosyl-1→6-sorbitol), GPM (α-D-glucopyranosyl-1→6-mannitol) and hydrogenated maltooligosaccharides and maltooligosaccharides.

14. The method according to claim 1, wherein the vacuum is initially about 30 mT with an initial temperature of about 40° C.

15. The method according to claim 1, wherein step c) further comprises the steps of i) holding the temperature at about 40° C. for about 16 hours; and ii) raising the temperature incrementally to about 80° C. at a rate of about 2.5° C. per minute at increment of about 2° C., wherein each increment is of a duration of about 12 minutes.

16. The method according to claim 1, where the glass form of the stabilizing agent in step c has a residual moisture that does not exceed about 2.5% (w/w).

17. The method according to claim 1 wherein the glass is a foamed glass matrix.

18. A composition obtained according to the method of claim 1.

19. The method according to claim 1, further comprising the step of: d) reconstituting the prokaryotic cells by adding a suitable solvent.

20. The method according to claim 19, wherein the solvent is aqueous.

21. A method for reconstituting dried, stabilized prokaryotic cells comprising adding a suitable solvent to the dried prokaryotic cells obtained in claim 1 in an amount sufficient to attain viability.

22. The method of claim 1, wherein intracellular production of trehalose is stimulated in the bacteria prior to drying.

23. A method of preserving prokaryotic cells comprising:
   a) increasing intracellular trehalose concentration in the prokaryotic cells to at least 30 mM;

b) mixing the prokaryotic cells obtained in step a) with a drying solution comprising a stabilizing agent, wherein the stabilizing agent is a carbohydrate; and c) drying the product of step b) under conditions sufficient to produce a glass form of the stabilizing agent having less than about 5% (w/w) residual moisture;

wherein the drying comprises evaporating the solution to obtain a syrup; exposing the syrup to a reduced external pressure and temperature sufficient to cause boiling of the syrup; and removing moisture so that residual moisture does not exceed about 5%;

wherein the prokaryotic cells retain greater than 50% viability upon drying; and wherein the prokaryotic cells are *Escherichia coli*.

* * * * *